(12) United States Patent
Narayanan

(10) Patent No.: US 6,780,642 B2
(45) Date of Patent: Aug. 24, 2004

(54) ASSOCIATION OF SIM2 WITH CANCER

(75) Inventor: Ramaswamy Narayanan, Delray Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 91 days.

(21) Appl. No.: 09/923,684

(22) Filed: Aug. 6, 2001

(65) Prior Publication Data

US 2002/0081613 A1 Jun. 27, 2002

Related U.S. Application Data

(60) Provisional application No. 60/257,965, filed on Dec. 22, 2000, and provisional application No. 60/223,531, filed on Aug. 4, 2000.

(51) Int. Cl.[7] ........................ C07H 21/04; C12N 15/00; A61K 31/70
(52) U.S. Cl. ..................... 435/375; 435/377; 536/23.1; 536/24.1; 536/24.5; 514/44
(58) Field of Search ............................ 435/6, 375, 377; 536/23.1, 24.1, 24.5; 514/44

(56) References Cited

PUBLICATIONS

DeYoung et al., PNAS. vol. 100(8):4760–4765, Apr. 15, 2003.*

Kong et al., FASEB Journal vol. 15(4): A762, Mar. 31, 2001.*

Agrawal et al., Molecular Medicine Today vol. 6:72–81, 2000.*

Sharma et al., BioEssays vol. 17(12):10551063.*

Chrast et al., " Cloning of Two Human Homologs of the Drosophila single–minded Gene SIM1 on Chromosome 6q and SIM2 on 21q Within the Down Syndrome Chromosomal Region," Genome Research, 7:615, 1997.

Muenke et al., "Physical Mapping of the Holoprosencephaly Critical Region in 21q22.3, Exclusion of SIM2 as a Candidate Gene for Holoprosencephaly, and Mapping of SIM2 to a Region of Chromosome 21 Important for Down Syndrome," Am. J. Genet, 57: 1074, 1995.

Meka et al., "Differential expression of hSim2 in prostate cancer," Proceedings of the American Association for Cancer Research, 40: 232, 1999.

* cited by examiner

*Primary Examiner*—Sean McGarry
(74) *Attorney, Agent, or Firm*—Edwards & Angell, LLP; Margaret J. McLaren, Esq.

(57) ABSTRACT

Disclosed are methods of detecting cancer in a biological sample by detecting SIM2 nucleic acid or protein in the sample. Also disclosed are methods for treating cancer and identifying compounds that modulate SIM2 expression.

16 Claims, 1 Drawing Sheet

US 6,780,642 B2

ASSOCIATION OF SIM2 WITH CANCER

CROSS REFERENCE TO RELATED APPLICATION

The present application claims the priority of U.S. provisional patent application No. 60/257,965 filed Dec. 22, 2000 and U.S. provisional patent application No. 60/223,531 filed Aug. 4, 2000.

FIELD OF THE INVENTION

The invention relates generally to the fields of molecular biology, genomics, bioinformatics, pathology, and medicine. More particularly, the invention relates to a new utility of a gene whose expression is modulated in select cancers.

BACKGROUND

Recent efforts to sequence the entire human genome have resulted in the identification of tens of thousands of genes. See, e.g., Venter et al., Science, 291:1304–51, 2001. Despite this achievement, many of these identified genes have yet to be functionally characterized. As the function of these genes are elucidated they should prove to be useful for identifying new diagnostic and therapeutic targets for a variety of different diseases.

SUMMARY

The invention relates to the discovery of specific polynucleotide sequences that are expressed at higher levels in select cancer cells than in non-diseased cells. The polynucleotide sequences were identified using a modified datamining tool referred to herein as DDDM (for Digital Differential Display tool, Modified) to analyze the Cancer Gene Anatomy Project (CGAP) database of the National Cancer Institute. In particular, DDDM was used to identify several expressed sequence tags (ESTs) more prevalent in cancer tissue libraries than in corresponding non-cancerous tissue libraries. The identified ESTs were than used to identify specific UniGenes associated with cancer. Based on the identified polynucleotide sequences, a gene termed SIM2 (for Single Minded homolog 2), whose expression is selectively upregulated in colon, prostate and pancreas tumors was identified.

The native human SIM2 gene has previously been cloned and sequenced. Chrast et al., Genome Res. 7: 615–624, 1997. Northern blot analyses indicated that several different species of mRNA are expressed from the SIM2 gene, including those of 2.7, 3, 4.4, and 6 kb. The multiple mRNAs are believed to be due to alternative splicing, overlapping transcription, or different utilization of 5' or 3' untranslated sequences. At least two different forms of the SIM2 gene have been characterized. The long form (GenBank ACC# U80456; SEQ ID NO: 1) is 3901 bp and codes for a protein of 667 amino acid with an apparent molecular weight of 74 kD. The short-form (GenBank ACC# U80457; SEQ ID NO: 2) is 2859 bp and codes for a protein of 570 amino acid with an apparent molecular weight of 64 kD. The N-termini of both the forms of SIM2 protein show extensive sequence identity to each other as well as to another member of the family, SIM1. The N-terminus of all of these proteins contains four recognized domains, namely, bHLH, PAS1, PAS2 and HST. These domains are often seen in transcription factors. The C-terminal ends of the proteins show some similarity, but also contain unique sequences.

SIM2 has previously been associated with Down's Syndrome, but not cancer.

Accordingly, the invention features a method for detecting a cancer in a tissue sample. This method includes the steps of: (a) providing the tissue sample; and (b) analyzing the tissue sample for the presence of a SIM2 marker. The presence of the SIM2 marker in the tissue sample indicates that the tissue sample contains a cancer. In this method, the tissue sample can be a colon tissue sample, a prostate tissue sample, or a pancreas tissue sample.

SIM2 markers utilized within the invention can be, e.g., a SIM2 nucleic acid such as a SIM2 mRNA or a native SIM2 nucleic acid. The native SIM2 nucleic acid can have a nucleotide sequence SEQ ID NO: 1 or SEQ ID NO: 2. The SIM2 marker can also be a SIM2 protein such as a native SIM2 protein, e.g., one having an amino acid sequence of SEQ ID NO: 3 or SEQ ID NO: 4.

In the foregoing method, the step of providing a tissue sample can include obtaining the tissue sample from a human subject; and the step of analyzing the tissue sample can include isolating RNA from the tissue sample, generating cDNAs from the isolated RNA, amplifying the cDNAs by PCR to generate a PCR product, and electrophoretically separating the PCR product to yield an electrophoretic pattern. The step of amplifying the cDNAs by PCR can be performed using an oligonucleotide primer, e.g., one that includes a nucleotide sequence of SEQ ID NOs: 7, 8, 15, and 16. Also in this method, the step of amplifying the cDNAs by PCR can be performed using a first oligonucleotide primer and a second oligonucleotide primer. The first oligonucleotide primer can include the nucleotide sequence of SEQ ID NOs: 7 or 15. The second oligonucleotide primer can include the nucleotide sequence of SEQ ID NOs: 8 or 16. In a particular embodiment of this method, the presence of a 472 base pair nucleic acid in the electrophoretic pattern indicates that the tissue sample contains a cancer.

Also in the foregoing method, the step of analyzing the tissue sample for the SIM2 nucleic acid can include contacting the tissue sample with an oligonucleotide probe that hybridizes under stringent hybridization conditions to a polynucleotide having a nucleic acid sequence of SEQ ID NO: 1, SEQ ID NO: 2, the complement of SEQ ID NO: 1, or the complement of SEQ ID NO: 2. For example, the oligonucleotide probe can include the nucleic acid of SEQ ID NO: 9. The oligonucleotide probe of this method can also include a detectable label.

In a variation of the foregoing method, the SIM2 marker is a SIM2 protein such as a native SIM2 protein (e.g., one having an amino acid sequence of SEQ ID NO: 3 or SEQ ID NO: 4). In this variation, the step of providing a tissue sample can include obtaining the tissue sample from a human subject, and the step of analyzing the tissue sample can include contacting at least a portion of the tissue sample with a probe that specifically binds to the SIM2 protein. The probe can include a detectable label and/or an antibody (e.g., an antibody that specifically binds to the peptide of SEQ ID NO: 14). In another variation of the method, the tissue sample includes a cell isolated from feces, urine, or peripheral blood.

In another aspect, the invention features a method of modulating SIM2 gene expression. This method includes the steps of: (a) providing a cell that expresses a SIM2 gene; and (b) introducing into the cell an agent that modulates the expression the SIM2 gene in the cell. The agent can be an oligonucleotide such as an antisense oligonucleotide. For example, an antisense oligonucleotide that hybridizes under stringent hybridization conditions to a polynucleotide that encodes a SIM2 protein can be used, as can an antisense oligonucleotide that is at least 18 nucleotides in length and includes a sequence that is a complement of a nucleic acid that encodes the SIM2 protein. For instance, the antisense oligonucleotide can include a nucleic acid sequence of SEQ ID NOs: 11 or 12.

Also within the invention is a method of identifying a test compound that modulates expression of a SIM2 gene in a cell. This method includes the steps of: (a) providing a cell expressing a SIM2 gene; (b) contacting the cell with the test compound; and (c) detecting a modulation in the expression of the SIM2 gene. Detecting the modulation indicates that the test compound modulates expression of the SIM2 gene. In this method, the cell can be derived from a colon tissue sample, a prostate tissue sample, or a pancreas tissue sample. Also in this method, the step of detecting the modulation in the expression of the SIM2 gene can include analyzing the cell for a change in the intracellular concentration of a SIM2 marker.

The invention additionally features a method for reducing the growth rate of a cancer includes a cell expressing a SIM2 protein. This method includes the step of: contacting the cell with an agent that inhibits the expression of the SIM2 protein in the cell.

The agent can an oligonucleotide such as an antisense oligonucleotide. For example, an antisense oligonucleotide that hybridizes under stringent hybridization conditions to a polynucleotide that encodes a SIM2 protein can be used, as can an antisense oligonucleotide that is at least 18 nucleotides in length and includes a sequence that is a complement of a nucleic acid that encodes the SIM2 protein. For instance, the antisense oligonucleotide can include a nucleic acid sequence of SEQ ID NOs: 11 or 12.

In variations of this method, the cancer can be a colon cancer, a prostate cancer, or a pancreas cancer. The cancer can also be in an animal such as a mammal.

In still another aspect, the invention features a kit for modulating expression of a SIM2 gene in a cell. The kit can include: an agent that modulates the expression of the SIM2 gene in the cell and instructions for using the agent to modulate the expression of the SIM2 gene in the cell.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

By the term "gene" is meant a nucleic acid molecule that codes for a particular protein, or in certain cases, a functional or structural RNA molecule. For example, the SIM2 gene encodes the SIM2 protein.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the terms "SIM2 gene," "SIM2 polynucleotide," or "SIM2 nucleic acid" is meant a native SIM2-encoding nucleic acid sequence, e.g., the native SIM2 gene; the native long form SIM2 cDNA (SEQ ID NO: 1); the native short form SIM2 cDNA (SEQ ID NO: 2); a nucleic acid having sequences from which a SIM2 cDNA can be transcribed; and/or allelic variants and homologs of the foregoing. The terms encompass double-stranded DNA, single-stranded DNA, and RNA.

As used herein, "protein" or "polypeptide" mean any peptide-linked chain of amino acids, regardless of length or post-translational modification, e.g., glycosylation or phosphorylation. A "purified" polypeptide is one that is substantially separated from other polypeptides in a cell or organism in which the polypeptide naturally occurs (e.g., 30, 40, 50, 60, 70, 80, 90, 95, 96, 97, 98, 99, 100% free of contaminants).

By the terms "SIM2 protein" or "SIM2 polypeptide" is meant an expression product of a SIM2 gene such as the native long form SIM2 protein (SEQ ID NO: 3), the native short form SIM2 protein (SEQ ID NO: 4), or a protein that shares at least 65% (but preferably 75, 80, 85, 90, 95, 96, 97, 98, or 99%) amino acid sequence identity with one of the foregoing and displays a functional activity of a native SIM2 protein. A "functional activity" of a protein is any activity associated with the physiological function of the protein. For example, functional activities of a native SIM2 protein may include DNA-binding activity and selective expression in certain neoplastic tissues.

When referring to a nucleic acid molecule or polypeptide, the term "native" refers to a naturally-occurring (e.g., a "wild-type") nucleic acid or polypeptide. A "homolog" of a SIM2 gene is a gene sequence encoding a SIM2 polypeptide isolated from an organism other than a human being. Similarly, a "homolog" of a native SIM2 polypeptide is an expression product of a SIM2 gene homolog.

As used herein, a "SIM2 marker" is any molecule whose presence in a sample (e.g., a cell) indicates that a SIM2 gene is expressed in the sample. SIM2 markers include SIM2 nucleic acids and SIM2 proteins. "Expressing a SIM2 gene" or like phrases mean that a sample contains a transcription product (e.g., messenger RNA, i.e., "mRNA") of a SIM2 gene or a translation product of a SIM2 protein-encoding nucleic acid (e.g., a SIM2 protein). A cell expresses a SIM2 gene when it contains a detectable level of a SIM2 nucleic acid or a SIM2 protein.

A "fragment" of a SIM2 nucleic acid is a portion of a SIM2 nucleic acid that is less than full-length and comprises at least a minimum length capable of hybridizing specifically with a native SIM2 nucleic acid under stringent hybridization conditions. The length of such a fragment is preferably at least 15 nucleotides, more preferably at least 20 nucleotides, and most preferably at least 30 nucleotides of a native SIM2 nucleic acid sequence. A "fragment" of a SIM2 polypeptide is a portion of a SIM2 polypeptide that is less than full-length (e.g., a polypeptide consisting of 5, 10, 15, 20, 30, 40, 50, 75, 100 or more amino acids of a native SIM2 protein), and preferably retains at least one functional activity of a native SIM2 protein.

When referring to hybridization of one nucleic acid to another, "low stringency conditions" means in 10% formamide, 5× Denhart's solution, 6× SSPE, 0.2% SDS at 42° C., followed by washing in 1× SSPE, 0.2% SDS, at 50° C.; "moderate stringency conditions" means in 50% formamide, 5× Denhart's solution, 5× SSPE, 0.2% SDS at 42° C., followed by washing in 0.2× SSPE, 0.2% SDS, at 65° C.; and "high stringency conditions" means in 50% formamide, 5× Denhart's solution, 5× SSPE, 0.2% SDS at 42° C., followed by washing in 0.1× SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute of one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with a another amino acid having similar characteristics. Examples of conservative amino acid substitutions are ser for ala, thr, or cys; lys for arg; gln for asn, his, or lys; his for asn; glu for asp or lys; asn for his or gln; asp for glu; pro for gly; leu for ile, phe, met, or val; val for ile or leu; ile for leu, met, or val; arg for lys; met for phe; tyr for phe or trp; thr for ser; trp for tyr; and phe for tyr.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors."

A first nucleic-acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic." A "transgenic" or "transformed" cell or organism also includes progeny of the cell or organism, including progeny produced from a breeding program employing such a "transgenic" cell or organism as a parent in a cross. For example, an organism transgenic for SIM2 is one in which SIM2 nucleic acid has been introduced.

By the term "SIM2-specific antibody" is meant an antibody that binds a SIM2 protein and displays no substantial binding to other naturally occurring proteins other than those sharing the same antigenic determinants as the SIM2 protein. The term includes polyclonal and monoclonal antibodies as well as antibody fragments.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

The term "labeled," with regard to a probe or antibody, is intended to encompass direct labeling of the probe or antibody by coupling (i.e., physically linking) a detectable substance to the probe or antibody.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. The particular embodiments discussed below are illustrative only and not intended to be limiting.

BRIEF DESCRIPTION OF THE DRAWINGS

The invention is pointed out with particularity in the appended claims. The above and the further advantages of this invention may be better understood by referring to the following description taken in conjunction with the accompanying drawings, in which:

DETAILED DESCRIPTION

Figure 1:
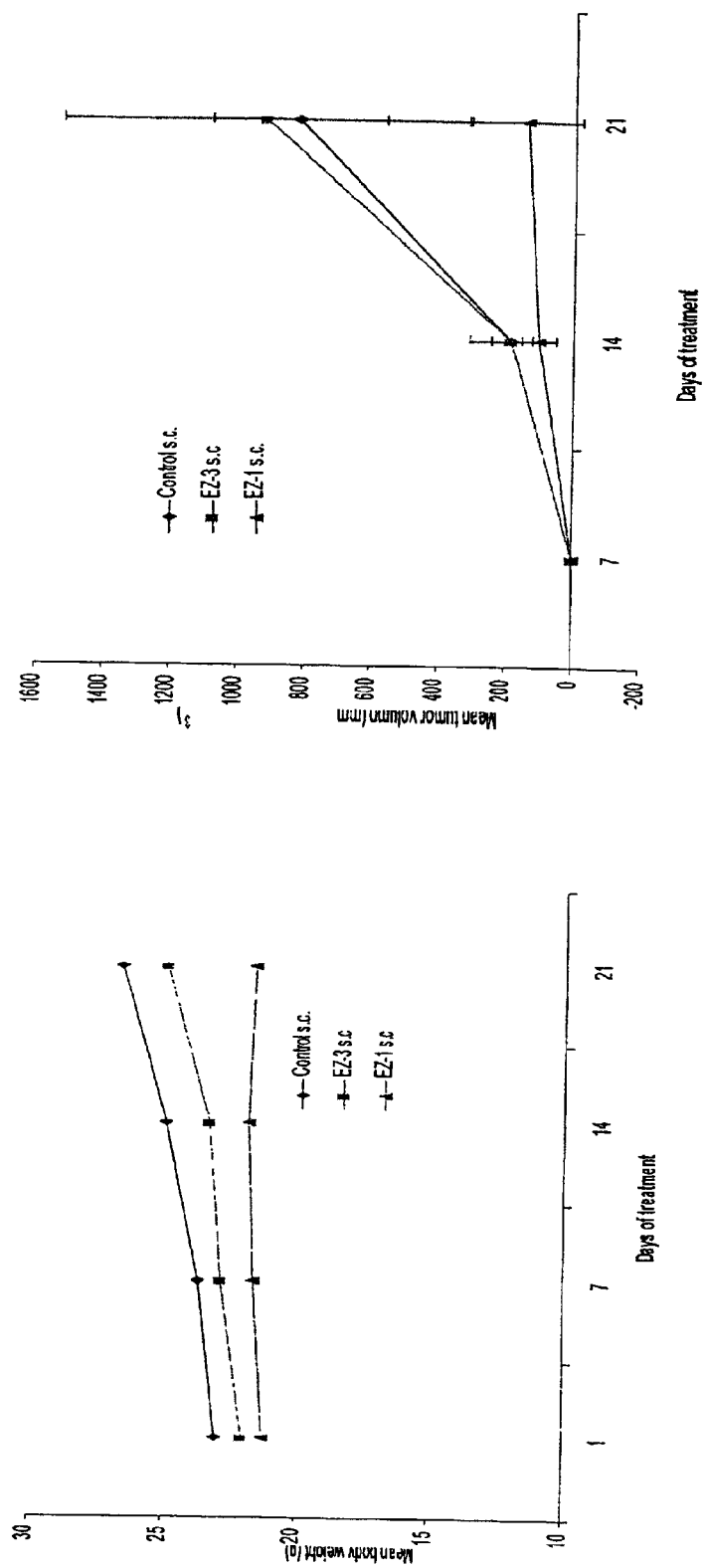
FIG. 1 is a series of two graphs showing the effect of a SIM2 antisense oligonucleotide on the growth of tumor cells in an animal model. E-Z-1 and E-Z-3 respectfully correspond to SEQ ID NOs: 12 and 13.

The invention encompasses compositions and methods relating to a gene whose expression is associated with cancer. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, ©1991, Whitehead Institute for Biomedical Research, Cambridge, Mass.). The Reverse Transcriptase Polymerase Chain Reaction (RT-PCR) method used to identify and amplify certain polynuleotide sequences within the invention was performed as described in Elek et al., In Vivo, 14:172–182, 2000). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Nucleic Acids Encoding SIM2 Proteins

Preferred nucleic acid molecules for use in the invention are the native SIM2 long form polynucleotide shown herein as SEQ ID NO: 1 and deposited with Genbank as Accession No. U80456 and the native SIM2 short form polynucleotide shown herein as SEQ ID NO: 2 and deposited with Genbank as Accession No. U80457. Another nucleic acid that can be used in various aspects of the invention includes a purified nucleic acid (polynucleotide) that encodes a polypeptide having the amino acid sequence of SEQ ID NOs: 3 or 4. As the native SIM2 gene was originally cloned from a human fetal kidney cDNA library, nucleic acid molecules encoding a polypeptide of the present invention can be obtained from such a library or from human fetal kidney tissue itself by conventional cloning methods such as those described herein.

Nucleic acid molecules utilized in the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes a native SIM2 protein may be identical to the nucleotide sequence of SEQ ID NOs: 1 or 2 or it may also be a different coding sequence which, as a result of the redundancy or degeneracy of the genetic code, encodes the same polypeptide as the polynucleotides of SEQ ID NOs: 1 or 2. Other nucleic acid molecules within the invention are variants of the native SIM2 gene such as those that encode fragments, analogs and derivatives of a native SIM2 protein. Such variants may be, e.g., a naturally occurring allelic variant of the native SIM2 gene, a homolog of the native SIM2 gene, or a non-naturally occurring variant of the native SIM2 gene. These variants have a nucleotide sequence that differs from the native SIM2 gene in one or more bases. For example, the nucleotide sequence of such variants can feature a deletion, addition, or substitution of one or more nucleotides of the native SIM2 gene. Nucleic acid insertions are preferably of about 1 to 10 contiguous nucleotides, and deletions are preferably of about 1 to 30 contiguous nucleotides.

In other applications, variant SIM2 proteins displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of a native SIM2 gene or native SIM2 mRNAs within the invention are nucleic acids isolated from human tissue that have at least 75% (e.g., 76%, 77%, 78%, 79%, 80%, 81%, 82%, 83%, 84%, 85%, 86%, 87%, 88%, 89%, 90%, 92%, 93%, 94%, 95%, 96%, 97%, 98%, and 99%) sequence identity with the native SIM2 gene or native SIM2 mRNAs, and encode polypeptides having structural similarity to a native SIM2 protein. Homologs of the native SIM2 gene or native SIM2 mRNAs within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native SIM2 gene or native SIM2 mRNAs, and encode polypeptides having structural similarity to native SIM2 protein. Public and/or proprietary nucleic acid databases can be searched to identify other nucleic acid molecules having a high percent (e.g., 70, 80, 90% or more) sequence identity to the native SIM2 gene or native SIM2 mRNAs.

Non-naturally occurring SIM2 gene or mRNA variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native SIM2 gene or native SIM2 mRNAs, and encode polypeptides having structural similarity to native SIM2 protein. Examples of non-naturally occurring SIM2 gene variants are those that encode a fragment of a SIM2 protein, those that hybridize to the native SIM2 gene or a complement of the native SIM2 gene under stringent conditions, those that share at least 65% sequence identity with the native SIM2 gene or a complement thereof, and those that encode a SIM2 fusion protein.

Nucleic acids encoding fragments of a native SIM2 protein within the invention are those that encode, e.g., 2, 5, 10, 25, 50, 100, 150, 200, 250, 300, or more amino acid residues of the native SIM2 protein. Shorter oligonucleotides (e.g., those of 6, 7, 8, 9, 10, 11, 12, 13, 14, 15, 16, 17, 18, 19, 20, 30, 50, 100, 125, 150 or 200 base pairs in length) that encode or hybridize with nucleic acids that encode fragments of a native SIM2 protein can be used as probes, primers, or antisense molecules. Longer polynucleotides (e.g., those of 300, 400, 500, 600, 700, 800, 900, 1000, 1100, 1200, 1300, 1400, 1500, 1600, 1700, or 1800 base pairs) that encode or hybridize with nucleic acids that encode fragments of a native SIM2 protein can also be used in various aspects of the invention. Nucleic acids encoding fragments of a native SIM2 protein can be made by enzymatic digestion (e.g., using a restriction enzyme) or chemical degradation of the full length native SIM2 gene, a SIM2 mRNA or cDNA, or variants of the foregoing.

Nucleic acids that hybridize under stringent conditions to the nucleic acid of SEQ ID NOs: 1 or 2 or the complement of SEQ ID NOs: 1 or 2 can also be used in the invention. For example, such nucleic acids can be those that hybridize to SEQ ID NOs: 1 or 2 or the complement of SEQ ID NOs: 1 or 2 under low stringency conditions, moderate stringency conditions, or high stringency conditions are within the invention. Preferred such nucleotide acids are those having a nucleotide sequence that is the complement of all or a portion of SEQ ID NOs: 1 or 2. Other variants of the native SIM2 gene within the invention are polynucleotides that share at least 65% (e.g., 65, 70, 75, 80, 85, 90, 91, 92, 93, 94, 95, 96, 97, 98, and 99%) sequence identity to SEQ ID NOs: 1 or 2 or the complement of SEQ ID NOs: 1 or 2. Nucleic acids that hybridize under stringent conditions to or share at least 65% sequence identity with SEQ ID NOs: 1 or 2 or the complement of SEQ ID NOs: 1 or 2 can be obtained by techniques known in the art such as by making mutations in the native SIM2 gene, or by isolation from an organism expressing such a nucleic acid (e.g., an allelic variant).

Nucleic acid molecules encoding SIM2 fusion proteins are also within the invention. Such nucleic acids can be made by preparing a construct (e.g., an expression vector) that expresses a SIM2 fusion protein when introduced into a suitable host. For example, such a construct can be made by ligating a first polynucleotide encoding a SIM2 protein fused in frame with a second polynucleotide encoding another protein such that expression of the construct in a suitable expression system yields a fusion protein.

The nucleic acid molecules of the invention can be modified at a base moiety, sugar moiety, or the phosphate backbone, e.g., to improve stability of the molecule, hybridization, etc. For example the nucleic acid molecules of the invention can be conjugated to groups such as peptides (e.g., for targeting host cell receptors in vivo), or agents facilitating transport across the cell membrane (see, e.g., Letsinger et al. (1989) Proc. Natl. Acad. Sci. U.S.A. 86:6553–6556; Lemaitre et al. (1987) Proc. Natl. Acad. Sci. USA 84:648–652; PCT Publication No. WO 88/09810, published Dec. 15, 1988), hybridization-triggered cleavage agents. (See, e.g., Krol et al. (1988) BioTechniques 6:958–976) or intercalating agents. (See, e.g, Zon (1988) Pharm. Res. 5:539–549).

Using the nucleotide sequence of the native SIM2 gene and the amino acid sequence of the native SIM2 protein previously reported, those skilled in the art can create nucleic acid molecules that have minor variations in their nucleotide sequence, by, for example, standard nucleic acid mutagenesis techniques or by chemical synthesis. Variant SIM2 nucleic acid molecules can be expressed to produce variant SIM2 proteins.

Antisense, Ribozyme, Triplex Techniques

Another aspect of the invention relates to the use of purified antisense nucleic acids to inhibit expression of SIM2. Antisense nucleic acid molecules within the invention are those that specifically hybridize (e.g. bind) under cellular conditions to cellular mRNA and/or genomic DNA encoding a SIM2 protein in a manner that inhibits expression of the SIM2 protein, e.g., by inhibiting transcription and/or translation. The binding may be by conventional base pair complementarity, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes a SIM2 protein. Alternatively, the antisense construct can take the form of an oligonucleotide probe generated ex vivo which, when introduced into a SIM2 protein expressing cell, causes inhibition of SIM2 protein expression by hybridizing with an mRNA and/or genomic sequences coding for SIM2 protein. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of a SIM2 protein encoding nucleotide sequence, are preferred.

Antisense approaches involve the design of oligonucleotides (either DNA or RNA) that are complementary to SIM2 mRNA. The antisense oligonucleotides will bind to SIM2 mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex or triplex. One skilled in the art can ascertain a tolerable degree of mismatch by use of standard procedures to determine the melting point of the hybridized complex. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. (Wagner, R. (1994) Nature 372:333). Therefore, oligonucleotides complementary to either the 5' or 3' untranslated, non-coding regions of a SIM2 gene could be used in an antisense approach to inhibit translation of endogenous SIM2 mRNA. Oligonucleotides complementary to the 5' untranslated region of the mRNA should preferably include the complement of the AUG start codon. Although antisense oligonucleotides complementary to mRNA coding regions are generally less efficient inhibitors of translation, these could still be used in the invention. Whether designed to hybridize to the 5', 3' or coding region of a SIM2 mRNA, preferred antisense nucleic acids are less that about 100 (e.g., less than about 30, 25, 20, or 18) nucleotides in length. Generally, in order to be effective, the antisense oligonucleotide should be 18 or more nucleotides in length. An exemplary antisense oligonucleotide is shown herein as SEQ ID NO: 11.

Specific antisense oligonucleotides can be tested for effectiveness using in vitro studies to assess the ability of the antisense oligonucleotide to inhibit gene expression. Preferably such studies (1) utilize controls (e.g., a non-antisense oligonucleotide of the same size as the antisense oligonucleotide) to distinguish between antisense gene inhibition and nonspecific biological effects of oligonucleotides, and (2) compare levels of the target RNA or protein with that of an internal control RNA or protein.

Antisense oligonucleotides of the invention may include at least one modified base or sugar moiety. Exemplary modified bases include 5-fluorouracil, 5-bromouracil, 5-chlorouracil, 5-iodouracil, hypoxanthine, xanthine, 4-acetylcytosine, 5-(carboxyhydroxyethyl) uracil, 5-carboxymethylaminomethyl-2-thiouridine, 5-carboxymethylaminomethyluracil, dihydrouricil, beta-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Exemplary modified sugar moieties include arabinose, 2-fluoroarabinose, xylulose, and hexose. The antisense oligonucleotides of the invention may in some embodiments include at least one modified phosphate backbone such as a phosphorothioate, a phosphorodithioate, a phosphoramidothioate, a phosphoramidate, a phosphordiamidate, a methylphosphonate, an alkyl phosphotriester, or a formacetal or analog thereof.

Antisense oligonucleotides within the invention might also be an alpha-anomeric oligonucleotide. See, Gautier et al. (1987) Nucl. Acids Res. 15:6625–6641. For example, the antisense oligonucleotide can be a 2'-0-methylribonucleotide (Inoue et al. (1987) Nucl. Acids Res. 15:6131–6148), or a chimeric RNA-DNA analogue (Inoue et al. (1987) FEBS Lett. 215:327–330).

Oligonucleotides of the invention may be synthesized by standard methods known in the art, e.g by use of an automated DNA synthesizer. Phosphorothioate oligonucleotides may be synthesized by the method of Stein et al. (1988) Nucl. Acids Res. 16:3209). Methylphosphonate oligonucleotides can be prepared by use of controlled pore glass polymer supports (Sarin et al. (1988) Proc. Natl. Acad. Sci. U.S.A. 85:7448–7451).

The invention also provides a method for delivering one or more of the above-described nucleic acid molecules into cells that express SIM2. A number of methods have been developed for delivering antisense DNA or RNA into cells. For instance, antisense molecules can be introduced directly into a cell by electroporation, liposome-mediated transfection, CaCl-mediated transfection, or using a gene gun. Modified nucleic acid molecules designed to target the desired cells (e.g., antisense oligonucleotides linked to peptides or antibodies that specifically bind receptors or antigens expressed on the target cell surface) can be used. To achieve high intracellular concentrations of antisense oligonucleotides (as may be required to suppress translation on endogenous mRNAs), a preferred approach utilizes a recombinant DNA construct in which the antisense oligonucleotide is placed under the control of a strong promoter (e.g., the CMV promoter).

Ribozyme molecules designed to catalytically cleave SIM2 mRNA transcripts can also be used to prevent translation of SIM2 mRNAs and expression of SIM2 proteins (See, e.g., Wright and Kearney, Cancer Invest. 19:495, 2001; Lewin and Hauswirth, Trends Mol. Med. 7:221, 2001; Sarver et al. (1990) Science 247:1222–1225 and U.S. Pat. No. 5,093,246). As one example, hammerhead ribozymes that cleave mRNAs at locations dictated by flanking regions that form complementary base pairs with the target mRNA might be used so long as the target mRNA has the following common sequence: 5'-UG-3'. See, e.g., Haseloff and Gerlach (1988) Nature 334:585–591. To increase efficiency and minimize the intracellular accumulation of non-functional mRNA transcripts, a ribozyme should be engineered so that the cleavage recognition site is located near the 5' end of the target SIM2 mRNA. Ribozymes within the invention can be delivered to a cell using a vector as described below.

Other methods can also be used to reduce SIM2 gene expression in a cell. For example, SIM2 gene expression can be reduced by inactivating or "knocking out" the SIM2 gene or its promoter using targeted homologous recombination. See, e.g, Kempin et al., Nature 389: 802 (1997); Smithies et al. (1985) Nature 317:230–234; Thomas and Capecchi (1987) Cell 51:503–512; and Thompson et al. (1989) Cell 5:313–321. For instance, a mutant, non-functional SIM2 gene variant (or a completely unrelated DNA sequence) flanked by DNA homologous to the endogenous SIM2 gene (either the coding regions or regulatory regions of the SIM2 gene) can be used, with or without a selectable marker and/or a negative selectable marker, to transfect cells that express SIM2 protein in vivo.

SIM2 gene expression might also be reduced by targeting deoxyribonucleotide sequences complementary to the regulatory region of the SIM2 gene (i.e., the SIM2 promoter and/or enhancers) to form triple helical structures that prevent transcription of the SIM2 gene in target cells. See generally, Helene, C. (1991) Anticancer Drug Des. 6(6): 569–84; Helene, C., et al. (1992) Ann. N.Y. Acad. Sci. 660:27–36; and Maher, L. J. (1992) Bioassays 14(12): 807–15. Nucleic acid molecules to be used in this technique are preferably single stranded and composed of deoxyribonucleotides. The base composition of these oligonucleotides should be selected to promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex. The potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

The antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Probes and Primers

The invention also provides oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by the polymerase chain reaction (PCR) or other conventional nucleic-acid amplification methods. Probes and primers within the invention are generally 15 nucleotides or more in length, preferably 20 nucleotides or more, more preferably 25 nucleotides, and most preferably 30 nucleotides or more. Preferred probes and primers are those that hybridize to a native SIM2 gene (or cDNA or mRNA) sequence (e.g., SEQ ID NOs: 1 or 2) under high stringency conditions, and those that hybridize to SIM2 gene homologs under at least moderately stringent conditions. Preferably, probes and primers according to the present invention have complete sequence identity with a native SIM2 nucleic acid sequence. However, probes differing from this sequence that retain the ability to hybridize to a native SIM2 gene sequence under stringent conditions may be designed by conventional methods and used in the invention. Primers and probes based on the SIM2 gene sequences disclosed herein can be used to confirm (and, if necessary, to correct) the disclosed SIM2 gene sequences by conventional methods, e.g., by re-cloning and sequencing a native SIM2 gene or cDNA. Particularly preferred primers for use in the invention are shown as SEQ ID NO: 7 and SEQ ID NO: 8. A particularly preferred oligonucleotide probe for use in the invention is shown as SEQ ID NO: 9.

SIM2 Proteins

In other aspects, the present invention utilizes a purified SIM2 protein encoded by a nucleic acid of the invention. A preferred form of SIM2 is a purified native SIM2 protein that has the deduced amino acid sequence of SEQ ID NOs: 3 or 4. Variants of native SIM2 proteins such as fragments, analogs and derivatives of native SIM2 proteins are also within the invention. Such variants include, e.g., a polypeptide encoded by a naturally occurring allelic variant of a native SIM2 gene, a polypeptide encoded by an alternative splice form of a native SIM2 gene, a polypeptide encoded by a homolog of a native SIM2 gene, and a polypeptide encoded by a non-naturally occurring variant of a native SIM2 gene.

SIM2 protein variants have a peptide sequence that differs from a native SIM2 protein in one or more amino acids. The peptide sequence of such variants can feature a deletion, addition, or substitution of one or more amino acids of a native SIM2 polypeptide. Amino acid insertions are preferably of about 1 to 4 contiguous amino acids, and deletions are preferably of about 1 to 10 contiguous amino acids. In some applications, variant SIM2 proteins substantially maintain a native SIM2 protein functional activity (e.g., association with cancer or ability to modulate transcription). For other applications, variant SIM2 proteins lack or feature a significant reduction in a SIM2 protein functional activity.

Where it is desired to retain a functional activity of native SIM2 protein, preferred SIM2 protein variants can be made by expressing nucleic acid molecules within the invention that feature silent or conservative changes. Variant SIM2 proteins with substantial changes in functional activity can be made by expressing nucleic acid molecules within the invention that feature less than conservative changes.

SIM2 protein fragments corresponding to one or more particular motifs and/or domains or to arbitrary sizes, for example, at least 5, 10, 25, 50, 75, 100, 125, 150, 175, 200, 250, 300, and 350 amino acids in length are within the scope of the present invention. Isolated peptidyl portions of SIM2 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a SIM2 protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a native SIM2 protein.

Another aspect of the present invention concerns recombinant forms of the SIM2 proteins. Recombinant polypeptides preferred by the present invention, in addition to native SIM2 protein, are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of SEQ ID NOs: 1 or 2. In a preferred embodiment, variant SIM2 proteins have one or more functional activities of native SIM2 protein.

SIM2 protein variants can be generated through various techniques known in the art. For example, SIM2 protein variants can be made by mutagenesis, such as by introducing discrete point mutation(s), or by truncation. Mutation can give rise to a SIM2 protein variant having substantially the same, or merely a subset of the functional activity of a native SIM2 protein. Alternatively, antagonistic forms of the protein can be generated which are able to inhibit the function of the naturally occurring form of the protein, such as by competitively binding to another molecule that interacts with SIM2 protein. In addition, agonistic forms of the protein may be generated that constitutively express on or more SIM2 functional activities. Other variants of SIM2 proteins that can be generated include those that are resistant to proteolytic cleavage, as for example, due to mutations which alter protease target sequences. Whether a change in the amino acid sequence of a peptide results in a SIM2 protein variant having one or more functional activities of a native SIM2 protein can be readily determined by testing the variant for a native SIM2 protein functional activity.

As another example, SIM2 protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential SIM2 protein sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. AG Walton, Amsterdam: Elsevier pp 273–289; Itakura et al. (1984) Annu. Rev. Biochem. 53:323;

Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) Proc. Natl. Acad. Sci. USA 89:2429–2433; Devlin et al. (1990) Science 249: 404–406; Cwirla et al. (1990) Proc. Natl. Acad. Sci. USA 87: 6378–6382; as well as U.S. Pat. Nos. 5,223,409; 5,198,346; and 5,096,815).

Similarly, a library of coding sequence fragments can be provided for a SIM2 gene clone in order to generate a variegated population of SIM2 protein fragments for screening and subsequent selection of fragments having one or more native SIM2 protein functional activities. A variety of techniques are known in the art for generating such libraries, including chemical synthesis. In one embodiment, a library of coding sequence fragments can be generated by (i) treating a double-stranded PCR fragment of a SIM2 gene coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with SI nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of SIM2 gene variants. The most widely used techniques for screening large gene libraries typically involve cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Combinatorial mutagenesis has a potential to generate very large libraries of mutant proteins, e.g., in the order of $10^{26}$ molecules. To screen a large number of protein mutants, techniques that allow one to avoid the very high proportion of non-functional proteins in a random library and simply enhance the frequency of functional proteins (thus decreasing the complexity required to achieve a useful sampling of sequence space) can be used. For example, recursive ensemble mutagenesis (REM), an algorithm that enhances the frequency of functional mutants in a library when an appropriate selection or screening method is employed, might be used. Arkin and Yourvan (1992) Proc. Natl. Acad. Sci. USA 89:7811–7815; Yourvan et al. (1992) Parallel Problem Solving from Nature, 2., In Maenner and Manderick, eds., Elsevier Publishing Co., Amsterdam, pp. 401–410; Delgrave et al. (1993) Protein Engineering 6(3): 327–331.

The invention also provides for reduction of SIM2 proteins to generate mimetics, e.g. peptide or non-peptide agents, that are able to disrupt binding of a SIM2 protein to other proteins or molecules with which the native SIM2 protein interacts. Thus, the mutagenic techniques described herein can also be used to map which determinants of SIM2 protein participate in the intermolecular interactions involved in, for example, binding of a SIM2 protein to other proteins which may function upstream (e.g., activators or repressors of SIM2 functional activity) of the SIM2 protein or to proteins or nucleic acids which may function downstream of the SIM2 protein, and whether such molecules are positively or negatively regulated by the SIM2 protein. To illustrate, the critical residues of a SIM2 protein which are involved in molecular recognition of, for example, the SIM2 protein or other components upstream or downstream of the SIM2 protein can be determined and used to generate SIM2 protein-derived peptidomimetics which competitively inhibit binding of the SIM2 protein to that moiety. By employing scanning mutagenesis to map the amino acid residues of a SIM2 protein that are involved in binding other extracellular proteins, peptidomimetic compounds can be generated which mimic those residues of a native SIM2 protein. Such mimetics may then be used to interfere with the normal function of a SIM2 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1: 1231), and beta-aminoalcohols (Gordon et al. (1985) Biochem. Biophys. Res. Commun. 126:419; and Dann et al. (1986) Biochem. Biophys. Res. Commun. 134:71). SIM2 proteins may also be chemically modified to create SIM2 protein derivatives by forming covalent or aggregate conjugates with other chemical moieties, such as glycosyl groups, lipids, phosphate, acetyl groups and the like. Covalent derivatives of SIM2 protein can be prepared by linking the chemical moieties to functional groups on amino acid side chains of the protein or at the N-terminus or at the C-terminus of the polypeptide.

The present invention further pertains to methods of producing the subject SIM2 proteins. For example, a host cell transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant SIM2 protein can be isolated from host cells using techniques known in the art for purifying proteins including ion-exchange chromatography, gel filtration chromatography, ultrafiltration, electrophoresis, and immunoaffinity purification with antibodies specific for such protein.

For example, after a SIM2 protein has been expressed in a cell, it can be isolated using any immuno-affinity chromatography. For instance, an anti-SIM2 antibody (e.g., produced as described below) can be immobilized on a column chromatography matrix, and the matrix can be used for immuno-affinity chromatography to purify the SIM2 protein from cell lysates by standard methods (see, e.g., Ausubel et al., supra). After immuno-affinity chromatography, the SIM2 protein can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, a SIM2 protein is expressed as a fusion protein containing an affinity tag (e.g., GST) that facilitates its purification.

SIM2-Protein Specific Antibodies

SIM2 proteins (or immunogenic fragments or analogs thereof) can be used to raise antibodies useful in the invention. Such proteins can be produced by recombinant techniques or synthesized as described above. In general, SIM2 proteins can be coupled to a carrier protein, such as KLH, as described in Ausubel et al., supra, mixed with an adjuvant, and injected into a host mammal. Antibodies produced in that animal can then be purified by peptide antigen affinity chromatography. In particular, various host animals can be immunized by injection with a SIM2 protein or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and *Corynebacterium parvum*.

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the SIM2 proteins described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Once produced, polyclonal or monoclonal antibodies can be tested for specific SIM2 recognition by Western blot or immunoprecipitation analysis by standard methods, for example, as described in Ausubel et al., supra. Antibodies that specifically recognize and bind to SIM2 are useful in the invention. For example, such antibodies can be used in an immunoassay to monitor the level of a SIM2 protein produced by a mammal (e.g., to determine the amount or subcellular location of a SIM2 protein).

Preferably, SIM2 protein selective antibodies of the invention are produced using fragments of the SIM2 protein that lie outside highly conserved regions and appear likely to be antigenic, by criteria such as high frequency of charged residues. Cross-reactive anti-SIM2 protein antibodies are produced using a fragment of SIM2 protein that is conserved amongst members of this family of proteins. In one specific example, such fragments are generated by standard techniques of PCR, and are then cloned into the pGEX expression vector (Ausubel et al., supra). Fusion proteins are expressed in *E. Coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant SIM2 proteins or control proteins, such as glucocorticoid receptor, CAT, or luciferase.

The antibodies of the invention can be used, for example, in the detection of a SIM2 protein in a biological sample. Antibodies also can be used in a screening assay to measure the effect of a candidate compound on expression or localization of a SIM2 protein. Additionally, such antibodies can be used to interfere with the interaction of a SIM2 protein and other molecules that bind the SIM2 protein.

Techniques described for producing single chain antibodies (e.g., U.S. Pat. Nos. 4,946,778, 4,946,778, and 4,704,692) can be adapted to make single chain antibodies against a SIM2 protein, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

Human or humanoid antibodies that specifically bind a SIM2 protein can also be produced using known methods. For example, polyclonal antibodies can also be collected from human subjects having such antibodies in their sera, e.g., subjects administered antigens that stimulate antibody production against a SIM2 protein. As another example, human antibodies against a SIM2 protein can be made by adapting known techniques for producing human antibodies in animals such as mice. See, e.g., Fishwild, D. M. et al., Nature Biotechnology 14 (1996): 845–851; Heijnen, I. et al., Journal of Clinical Investigation 97 (1996): 331–338; Lonberg, N. et al., Nature 368 (1994): 856–859; Morrison, S. L., Nature 368 (1994): 812–813; Neuberger, M., Nature Biotechnology 14 (1996): 826; and U.S. Pat. Nos. 5,545, 806; 5,569,825; 5,877,397; 5,939,598; 6,075,181; 6,091, 001; 6,114,598; and 6,130,314. Humanoid antibodies against a SIM2 can be made from non-human antibodies by adapting known methods such as those described in U.S. Pat. Nos. 5,530, 101; 5,585,089; 5,693,761; and 5,693,762.

Proteins That Associate With SIM2

The invention also features methods for identifying polypeptides that can associate with a SIM2 protein. Any method that is suitable for detecting protein-protein interactions can be employed to detect polypeptides that associate with a SIM2 protein. Examples of such methods include co-immunoprecipitation, crosslinking, and co-purification through gradients or chromatographic columns of cell lysates or proteins obtained from cell lysates and the use of SIM2 protein to identify proteins in the lysate that interact with a SIM2 protein. For these assays, the SIM2 protein can be a full length SIM2 protein, a particular domain of SIM2 protein, or some other suitable SIM2 protein. Once isolated, such an interacting protein can be identified and cloned and then used, in conjunction with standard techniques, to alter the activity of the SIM2 protein with which it interacts. For example, at least a portion of the amino acid sequence of a protein that interacts with SIM2 protein can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel et al., supra; and "PCR Protocols: A Guide to Methods and Applications," Innis et al., eds. Academic Press, Inc., NY, 1990).

Additionally, methods can be employed that result directly in the identification of genes that encode proteins that interact with a SIM2 protein. These methods include, for example, screening expression libraries, in a manner similar to the well known technique of antibody probing of lgt11 libraries, using labeled SIM2 protein or a SIM2 fusion protein, for example, a SIM2 protein or domain fused to a marker such as an enzyme, fluorescent dye, a luminescent protein, or to an IgFc domain.

There are also methods available that can detect protein-protein interaction in vivo. For example, as described herein the two-hybrid system can be used to detect such interactions in vivo. See, e.g., Chien et al., Proc. Natl. Acad. Sci. USA 88:9578, 1991. Briefly, as one example of utilizing such a system, plasmids are constructed that encode two hybrid proteins: one plasmid includes a nucleotide sequence encoding the DNA-binding domain of a transcription activator protein fused to a nucleotide sequence encoding a SIM2 protein, a SIM2 protein variant, or a SIM2 fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, a SIM2 protein may be used as the bait. Total genomic or cDNA sequences are fused to the DNA encoding an activation domain. This library and a plasmid encoding a hybrid of bait SIM2 protein fused to the DNA-binding domain are co-transformed into a yeast reporter strain, and the resulting transformants are screened for those that express the reporter gene. For example, a bait SIM2 gene sequence, such as that encoding a SIM2 protein or domain of a SIM2 protein can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait SIM2 protein are to be detected can be made using methods routinely practiced in the art. According to the particular system described herein, for example, the cDNA fragments can be inserted into a vector such that they are translationally fused to the transcriptional activation domain of GAL4. This library can be co-transformed along with the SIM2-GAL4 encoding fusion plasmid into a yeast strain which contains a lacZ gene driven by a promoter which contains GAL4 activation sequence. A cDNA encoded protein, fused to GAL4 transcriptional activation domain, that interacts with bait SIM2 protein will reconstitute an active GAL4 protein and thereby drive expression of the HIS3 gene. Colonies that express HIS3 can then be purified from these strains and used to produce and isolate bait SIM2 protein-interacting proteins using techniques routinely practiced in the art.

Detection of SIM2 Polynucleotides and Proteins

The invention encompasses methods for detecting the presence of a SIM2 protein or a SIM2 nucleic acid in a biological sample as well as methods for measuring the level of a SIM2 protein or a SIM2 nucleic acid in a biological sample. Such methods are useful for diagnosing cancer associated with SIM2 expression (e.g., colon cancer).

An exemplary method for detecting the presence or absence of a SIM2 protein or nucleic acid in a biological sample involves obtaining a biological sample from a test subject (e.g., a human patient), contacting the biological sample with a compound or an agent capable of detecting a SIM2 protein or a nucleic acid encoding a SIM2 protein (e.g., mRNA or genomic DNA), and analyzing binding of the compound or agent to the sample after washing. Those sample having specifically bound compound or agent express a SIM2 protein or a nucleic acid encoding a SIM2 protein.

A preferred agent for detecting a nucleic acid encoding a SIM2 protein is a labeled nucleic acid probe capable of hybridizing to the nucleic acid encoding the SIM2 protein. The nucleic acid probe can be, for example, all or a portion of a SIM2 gene itself (e.g., a nucleic acid molecule having the sequence of SEQ ID NOs: 1 or 2) or all or a portion of a complement of a SIM2 gene. Similarly, the probe can also be all or a portion of a SIM2 gene variant, or all or a portion of a complement of a SIM2 gene variant. For instance, oligonucleotides at least 15, 30, 50, 100, 250, or 500 nucleotides in length that specifically hybridize under stringent conditions to a native SIM2 nucleic acid or a complement of a native SIM2 nucleic can be used as probes within the invention. A preferred probe has the nucleotide sequence of SEQ ID NO: 9. A preferred agent for detecting a SIM2 protein is an antibody capable of binding to a SIM2 protein, preferably an antibody with a detectable label. Such antibodies can be polyclonal, or more preferably, monoclonal. An intact antibody, or a fragment thereof (e.g., Fab or F(ab')$_2$) can be used.

Detection methods of the invention can be used to detect an mRNA encoding a SIM2 protein, a genomic DNA encoding a SIM2 protein, or a SIM2 protein in a biological sample in vitro as well as in vivo. For example, in vitro techniques for detection of mRNAs encoding a SIM2 protein include PCR amplification methods, Northern hybridizations, and in situ hybridizations. In vitro techniques for detection of a SIM2 protein include enzyme linked immunosorbent assays (ELISAs), Western blots, immunoprecipitations and immunofluorescence. In vitro techniques for detection of genomic DNA encoding SIM2 include Southern hybridizations. Furthermore, in vivo techniques for detection of a SIM2 protein include introducing a labelled anti-SIM2 antibody into a biological sample or test subject. For example, the antibody can be labeled with a radioactive marker whose presence and location in a biological sample or test subject can be detected by standard imaging techniques.

Screening for Compounds that Interact with SIM2 Protein

The invention also encompasses methods for identifying compounds that specifically bind to a SIM2 protein. One such method involves the steps of providing immobilized purified SIM2 protein and at least one test compound; contacting the immobilized protein with the test compound; washing away substances not bound to the immobilized protein; and detecting whether or not the test compound is bound to the immobilized protein. Those compounds remaining bound to the immobilized protein are those that specifically interact with the SIM2 protein.

EXAMPLES

The present invention is further illustrated by the following specific examples. The examples are provided for illustration only and should not to be construed as limiting the scope of the invention in any way.

Example 1

Identifying Tumor-Associated ESTs by Datamining the CGAP Database Using DDDM

The CGAP database was accessed (http://www.cgap.gov) and the Digital Differential Display (DDD) tool was used according to the database instructions modified as described herein. DDD uses the UniGene database to compare the number of times ESTs from different libraries are assigned to a particular UniGene cluster. Known hits were classified into major families using information generated from two web sites (http://www.ncbi.nlm.nih.gov/Omim/) and the GeneCards site (http://bioinformatics.weizmann.ac.il/cards/). Novel ESTs were compiled into a separate database, and the UniGene database was accessed to establish an electronic expression profile (E-Northern) in order to predict the presence or absence of a given EST in a given tissue-derived cDNA library for each of the hits to facilitate tumor and organ selective gene discovery.

Six different solid tumor-derived EST libraries (breast, colon, lung, ovary, pancreas and prostate) with corresponding normal tissue derived libraries were chosen for DDD (N=110). To identify tumor and organ specific ESTs, all the other organ and tumor-derived EST libraries (N=327) were chosen for comparison with each of the six tumor types. The nature of the libraries (normal, pre-tumor or tumor) was authenticated by comparing the CGAP data with the Uni-Gene (http://www.ncbi.nlm.nih.gov/UniGene/) database. Those few libraries showing discrepancies of definition between the two databases were excluded.

The DDD was performed for each organ type individually. DDD was performed using ESTs from tumors (Pool A) and corresponding normal organ (Pool B) for the DDD2 method or tumors (Pool A) and all other organ and tumor-derived cDNA libraries including the corresponding normal (Pool B) for the DDD1 method using the online tool. The output provided a numerical value in each pool denoting the fraction of sequences within the pool that mapped to the UniGene cluster and a dot intensity corresponding to the numerical value. DDDM was employed to calculate the fold differences between the libraries being compared from this data. For a detailed description of DDDM, see, U.S. Provisional Patent Application No. 60/200,292, filed Apr. 28, 2000. The numerical value obtained from DDDM analysis was expressed as a ratio of pool A/pool B. As illustrated in the examples described below, DDDM analysis resulted in rapid identification of ESTs that were predicted to be exclusively present or absent in the tumors.

Example 2

Reverse Transcriptase Polymerase Chain Reaction (RT-PCR) Analysis

RT-PCR was performed on tumor and normal tissues obtained from the Cooperative Human Tissue Network (CHTN, Birmingham, Ala.). Total RNA was isolated by Trizol (Life Technologies, Gaithersburg, Md.)(See, Eleket al., In Vivo, 14:172–182, 2000). One microgram of total RNA was reverse transcribed using random hexamers and Superscipt Reverse Transcriptase (Life Technologies). One fortieth of the cDNA was PCR-amplified using gene-specific primers. PCR primers were designed using the Primer 3 program on the world wide web (http://www-genome.wi.mit.edu//cgi-bin/primer/primer3_www.cgi). The primer selection parameters were: (1) size of the primers=20–24 bp; (2) annealing temperature=60–65° C.; (3) GC content=minimum 50%; (4) self complementarity=none; and (5) homology to non redundant ESTs=none. Each PCR primer sequence was validated against the NCBI EST database using a BLAST algorithm to ensure 100% homology to the chosen EST sequence.

For detection of the SIM2 short-form nucleic acid (SEQ ID NO: 2), PCR primers having the sequence shown herein as SEQ ID NOs: 14 (sense) and 15 (antisense) were selected. In other cases, SIM2 was detected using PCR primers having the sequence shown herein as SEQ ID NOs: 7 (sense) and 8 (antisense). The PCR parameters included 94° C. for 7 m followed by a 35–40 cycle amplification at 94° C., 45 s; 62° C., 45 s; and 72° C., 90 s, with a final extension at 72° C. for 10 m done in a Perkin Elmer 9600. RT-minus controls and genomic DNA controls were routinely used to authenticate the RT-derived products (see, e.g, Elek et al., Anticancer Res, 20: 53–58, 2000). One half of the amplified products were separated by electrophoresis on a 2% agarose gel and detected by ethidium bromide staining of the gel. PCR-amplified products were confirmed by hybridization to an end-labeled internal oligonucleotide probe. To authenticate the quality of RNA, an internal control actin RT-PCR was simultaneously performed on all samples.

Example 3

RT-PCR Validation of Colon Specific ESTs

Colon-specific ESTs identified by DDDM were selected for RT-PCR validation of expression specificity in tissue samples. Primers were designed as described in Example 2. Random primed cDNAs from one matched set of normal and colon tumor were generated using Reverse Transcriptase (RT) and were analyzed for each of the identified 17 ESTs (See, Elek et al., In Vivo, 14:172–182, 2000). Among the seventeen ESTs analyzed, one belonging to Unigene Hs.# 146186 was present in the colon tumor tissues, but not in the normal tissue. In these experiments, Unigene # 146186 showed a RT-dependant PCR product of 472 bp (See SEQ ID NO: 10). This product was not seen in the control RT-minus reaction. UniGene # 146186 has seven ESTs assigned to the cluster. The sequence of the longest EST (Genbank Accession #AI 7333801) in this UniGene is 541 bp in length (SEQ ID NO: 5), which was extendable as a contig of 1001 bp (SEQ ID NO: 6). Alignment of this contig sequence against the nucleotide sequence database indicated a very high homology to a gene called Single minded gene 2 (SIM2; GenBank Accession No. U80456). The SIM2 gene maps to the Down's Syndrome chromosomal locus at chromosome 21 (21q 22.2) and is a suspected transcription factor. SIM2 protein is developmentally regulated and shows very restricted expression in fetal and adult tissues, in particular kidney, but not in most other normal tissues (Chrast et al., Genome Research, 7:615–624, 1997). It is likely that SIM2 gene is a transcription factor because it possesses known dimerization motifs. The C-terminus of the SIM2 gene codes for serine/threonine/proline rich regions that are found in both transcriptional repressors and activators. And as the C-terminal portion of the SIM2 gene diverge from other known transcriptional activators (such as Helix Loop Helix and PAS proteins), it is predicted that the SIM2 gene is a transcriptional repressor (Chrast et al., Genome Research, 7:615–624, 1997).

SIM2 protein expression is developmentally regulated and shows very restricted expression in fetal and adult tissues, in particular kidney, but not in most other normal tissues (Chrast et al., Genome Research, 7:615–624, 1997). It is believed to be a critical gene for the development of the Down's Syndrome, but was not associated with cancer. A protein encoded by the SIM2 gene acts in concert with other protein factors to both activate and repress transcription of a variety of genes.

In the experiments of this Example, the nucleic acids of SEQ ID NO: 7 (sense) and SEQ ID NO: 8 (antisense) were used as RT-PCR primers to compare expression of SIM2 from a matched set tumor and normal tissues. The cDNAs were made in the absence or presence of reverse transcriptase and were PCR-amplified using the nucleic acids SEQ ID NOs: 7 and 8 as primers. After amplification, the products were subjected to agarose gel electrophoresis. The gel was stained with ethidinum bromide and bands corresponding to nucleic acids were visualized using UV illumination. Consistent with the electronic prediction, an amplified product of 472 bp was detected in colon tumor tissue but not in normal colon tissue. The PCR product was RT-dependent.

Example 4

Detection of a SIM2 Gene by Hybridization Using an Oligonucleotide Probe

A SIM2 gene was detected using of an oligonucleotide probe labeled with $^{32}$P-dNTP. An oligonucleotide corresponding to SEQ ID NO: 9 was synthesized, and then end-labeled with gamma $^{32}$P-dATP using polynucleotide kinase. RT-PCR products were generated in the presence or absence of RT from a matched set of eight different tumor and normal colon tissue samples, transferred to a nitrocellulose membrane, and hybridized to the $^{32}$P-labeled oligonucleotide probe. This probe hybridized to a 472 bp product in the tumor-derived cDNAs, but not in the normal tissue cDNAs.

Example 5

Lack of SIM2 Expression in Diverse Normal Human Tissues

In order to evaluate the specificity of expression of SIM2 gene in colon tissues, a panel of cDNAs from diverse normal human tissues was obtained from Clontech Laboratories (Palo Alto, Calif.). These cDNAs were PCR amplified using the sense and the antisense primers described respectively as SEQ ID NOs: 7 and 8. RT-PCR analysis of these cDNAs was performed as described herein. The SIM2 gene was detected in kidney and tonsil, but not in heart, brain, placenta, liver, skeletal muscle, spleen, thymus, testis, peripheral blood lymphocytes, lymph nodes, bone marrow, fetal liver, breast, colon, lung, ovary, pancreas and prostate. The samples were simultaneously analyzed for actin expression as an internal control.

Example 6

SIM2 Gene Expression in Non-Colon Derived Solid Tumors

To further evaluate the specificity of SIM2 expression to colon tumors, random primed cDNAs from five other solid tumors (breast, lung, ovary, prostate and pancreas) were generated using the RT method described herein. These cDNAs were PCR amplified using the sense and the antisense primers described as SEQ ID NOs: 7 and 8. The amplified products were detected in colon, prostate and pancreas tumors, but not in breast, lung or ovary tumors. The samples were simultaneously analyzed for actin expression as an internal control.

Example 7

Identification of Cell Culture Models to Facilitate Drug Discovery for Cancers

The expression of SIM2 in cell lines derived from colon (SW-480, HCT-116, RKO, and OM-1), pancreas (CAPAN-1, CAPAN-2, HPAC, and BxPc3) and prostate (LN-CAP, DU-CAP, and PC-3) cancers was investigated. cDNAs were made from all lines and amplified by RT-PCR using SEQ ID NOs: 7 and 8 primers. After amplification, the products were subjected to agarose gel electrophoresis. The gel was stained with ethidinum bromide and bands corresponding to nucleic acids were visualized using UV illumination. SIM2 expression was detected in all the different cell lines representing all three tumor types.

Example 8

Colon Tumor-Specific Upregulation of a SIM2 Gene

Further evidence that the SIM2 gene expression is colon tumor specific was obtained using cDNAs derived from fourteen different matched normal and tumor colon tissues. Random primed cDNAs were generated from the total RNAs from these tissues, and the cDNAs were PCR amplified using the sense and the antisense primers described in SEQ ID NOs: 7 and 8. After amplification, the products were subjected to agarose gel electrophoresis. The products were then transferred to nitrocellulose and hybridized with a $^{32}$P-labeled oligonucleotide probe (SEQ ID NO: 9) that specifically hybridizes to the SIM2 gene. The results showed that the SIM2 gene was upregulated in each of the colon tumor tissues, but not in the matched normal tissues.

Example 9

Detection of SIM2 Expression in Early Stage Colon Tumors

SIM2 gene expression was analyzed using cDNAs derived from early stages of colon tumor including polyps, adenomas and carcinomas isolated from human subjects. Random primed cDNAs were generated from the total RNAs from these tissues and the cDNAs were PCR amplified using the sense and the antisense primers described in SEQ ID NOs: 7 and 8. After amplification, the products were subjected to agarose gel electrophoresis. SIM2 expression was detected in the polyp, adenoma, and carcinoma tissue samples analyzed, but was not detected in normal colon tissue. The use of the probe described in Example 8 or similar probes to detect expression of the SIM2 gene in early stage (e.g., pre-cancerous stages) colon neoplasms such as polyps or adenomas is specifically envisioned.

Example 10

Prostate Tumor-Specific Upregulation of The SIM2 Gene

SIM2 gene expression was also detected in prostate tumors isolated from human subjects and prostate tumor-derived cell lines. Random primed cDNAs were generated from the total RNAs from prostate tumor, benign prostatic hyperplasia (BPH) and normal tissues, and the cDNAs were PCR-amplified using the sense and the antisense primers described in SEQ ID NOs: 7 and 8. After amplification, the products were subjected to agarose gel electrophoresis. The gel was stained with ethidinum bromide and bands corresponding to nucleic acids were visualized using UV illumination. The results showed that the SIM2 gene expression was detected in the cell lines, BPH and in the tumors, but not in the normal prostate.

Example 11

Diagnostic Process

Evaluation of SIM2 gene expression is specifically envisioned as a method for diagnosing cancer. In this method, tissue to be examined is isolated from a patient (e.g., cells from polyps, adenomas carcinomas, etc. are obtained during routine colonoscopy). Total RNA obtained from these cells is then converted into cDNAs using either random primers or oligo dT to initiate the cDNA. The cDNAs obtained are PCR-amplified using the sense and the antisense primers described herein as SEQ ID NOs: 7 and 8. The PCR-amplified products are then subjected to agarose gel electrophoresis, and the gel is stained to visualize the nucleic acid bands. The presence of a 472 bp product is indicative of potential cancer.

Example 12

Detection of the SIM2 Gene by Hybridization

Using hybridization techniques, SIM2 gene expression can be detected with the oligonuc-leotide probe described herein as SEQ ID NO: 9. The oligonucleotide is labeled with a radioactive or non-radioactive label, and the labeled probe is reacted with RNA from the sample being analyzed in the form of a Northern blot by transferring the products onto a filter (for example, nitrocellulose). This method can also be performed in the form of a Southern blot of RT-PCR reaction products made from the genomic DNA contained in a sample being analyzed. Following hybridization to the oligonucleotide probe, the filter is washed, exposed to X-ray film, and autoradiographed. Bands that hybridize to the probe can be identified from the autoradiogram. The oligonucleotide probe can also be used for in situ hybridization reactions to directly detect SIM2 gene expression in tissues.

Example 13

Detection of Metastatic Cancer Cells

A method for detecting metastatic cancer cells is specifically envisioned. The method involves obtaining a tissue sample from a test subject (e.g., a cancer patient), optionally isolating nucleic acid (e.g., by PCR amplification) or protein from the sample, probing the sample or isolated nucleic acid/protein with a molecule that specifically binds to SIM2 genomic DNA, mRNA or cDNA, or the corresponding polypeptide product (e.g., a SIM2 protein). For example, in one variation of this method, total RNA is isolated from cancer cells obtained from fecal or peripheral blood samples. The RNA is then analyzed for the presence of SIM2 mRNA by RT-PCR using the oligonucleotides of SEQ ID NOs: 7 and 8 as primers. As another example, SIM2 gene expression can be detected in the cells of these samples by in situ hybridization using SEQ ID NO: 9 as a oligonucleotide probe. As still another example, antibodies specific for SIM2 protein can be used to probe cells samples directly (e.g., using conventional immunofluorescence, histochemical staining techniques) or can be used to detect SIM2 protein protein by immunoprecipitation and electrophoresis, or by Western blotting. Since SIM2 expression was also detected in tumor pancreas samples, but not in normal pancreas samples, metastatic pancreas tumor cells shed in the feces can also be detected by this method.

Example 14

SIM2 as a Therapeutic Target

The SIM2 gene product has a known function. It is a DNA-binding transcription factor and acts in concert with other protein factors as a heterodimer to regulate other genes involved in growth control. See, e.g., Yamaguchi and Kuo, Biochemical Pharmacol. 50, 1295–1302, 1995; and Moffet et al., J. Mol. Cell Biology, 17, 4933–4947, 1997. The SIM2 protein shares homology to the Aryl hydrocarbon receptor (AHR) and aryl hydrocarbon receptor nuclear translocator (ARNT). SIM2 proteins are cytosolic and interact with AHR and ARNT as well as proteins such as heat shock protein (HSP90). This interaction forms a complex that can bind to ligands such as dioxins, benzo(a)pyrenes, and other xenobiotics. Upon binding to a ligand, the complex is translocated to the nucleus, and causes activation of the Xenobiotic Response Element (XRE), a control element involved in transcriptional regulation of various target genes. Yamaguchi Y and Kuo M T, Biochemical Pharmacol. 50, 1295–1302, 1995.

Inhibition of SIM2 gene expression may thus be able to ameliorate a carcinogen's effects. In addition, because SIM2 is selectively expressed in certain cancers, it is thought to be a potential target for anti-neoplastic agents. Inhibition of SIM2 gene expression can be accomplished using an antisense nucleic acid. For example, a suitable length (e.g., 18–25 bases) of an antisense nucleic acid that specifically hybridizes to the 5' prime-coding region of a SIM2 gene is synthesized, and then introduced into target tissues or cells (e.g., by electroporation or delivery via a vector) or liposomes. The target tissues or cells are then placed under conditions that allow the anti-sense nucleic acid to hybridize to the mRNAs transcribed from the SIM2 gene. This hybridization prevents translation and thereby selectively inhibits expression of SIM2 protein. See, e.g., Narayanan, R. In Vivo, 8: 787–794, 1994. As another example, the foregoing antisense nucleic acid can also generated as a stable recombinant construct that can be delivered in vivo for gene therapy. See, e.g., Higgins et al., Proc Nat'l Acad Sci USA 90: 9901–9905, 1993.

In one variation of this example, the antisense nucleic acid is the oligonucleotide shown as SEQ ID NO: 11. This oligonucleotide can be substituted with various components at the nucleic acid backbone. Tumor-bearing patients can be treated with suitable formulations of this antisense oligonucleotide using methods similar to those described in Narayanan R and Akhtar S., Curr Opin Oncol 8: 509–515, 1996; Higgins et al., Proc Nat'l Acad Sci USA 90: 9901–9905, 1993; and Narayanan R, J. Nat'l. Cancer Inst. 89: 107–109, 1997. The antisense oligonucleotide can be used alone or in combination with conventional chemotherapy or radiotherapy protocols.

Example 15

SIM2 as a Drug Discovery Target

A method of discovering drugs that selectively inhibit SIM2 gene function is envisioned. SIM2 protein is thought to function by modulating the expression of particular genes via binding DNA at a regulatory region associated with the particular genes to control transcription. This characteristic can be exploited to screen for substances that inhibit SIM2 protein binding to DNA, and therefore inhibit this function of SIM2 protein. In this method, an expression vector incorporating a SIM2 gene is introduced into and expressed in a host cell under conditions that cause SIM2 protein to be produced in the cell. The SIM2 protein produced in this manner is then purified so that it can be used in an in vitro high throughput assay to screen for compounds that inhibit its ability to bind a particular stretch of DNA. See, e.g., Ruben et al., Mol. Cell Biol. 12: 444–454, 1992; Narayanan et al., Science 256: 367–370, 1992; and Narayanan et al., Mol Cell Biol 13: 3802–3810, 1993.

Inhibitors of SIM2 expression can also be identified using SIM2-expressing tumor-derived cell lines in growth inhibition assays. For example, a substance to be screened can be added to a culture containing a cell expressing SIM2 to see if the substance modulates SIM2 expression. In an alternative method, cell lines transfected with recombinant constructs containing a reporter gene (e.g., those that encode chloramphenicol acetyltransferase, luciferase, beta-galactosidase, etc.) operably linked to the SIM2 promoter can be used to identify substances that inhibit expression of the SIM2 gene. For example, compounds that selectively inhibit expression of the reporter would be identified as a SIM2-selective inhibitor.

As SIM2 is selectively expressed in colon, prostate and pancreas tumors; but not in breast, lung or ovary tumors, compounds can be screened for the ability to selectively inhibit growth of SIM2-expressing tumors. Compounds identified in this manner can be further evaluated for SIM2-specific inhibition using the SIM2 promoter-reporter gene constructs described above.

Example 16

Antibody Detection of SIM2 Protein

Tumor selective expression of a SIM2 gene product can be detected by measuring expression of a SIM2 protein using such techniques as immunohistochemistry or immunoflorescence. As an example of the latter technique, paraffin-fixed sections of colon tumor and corresponding normal tissues were analyzed using antibodies specific for the c-terminus of the SIM2 short-form protein (an affinity-purified rabbit anti-human SIM2 short-form antibody, Cat# sc-8715, Santa Cruz Biotechnology, Santa Cruz, Calif.) or the antibody prepared as described below in Example 17. Immunohistochemical detection of SIM2 protein was performed as described in Scheurle et al., Anticancer. Res. 20:2091–2096, 2000. In brief, the sections were deparaffinized in a xylene bath two times for five minutes, and then rehydrated through graded alcohols to distilled water. Slides were incubated with the primary anti-SIM2 short-form antibody. Bound primary antibody was detected by staining the sections with a horseradish peroxidase-labeled dextran polymer conjugated affinity-purified goat anti-rabbit immunoglobulin secondary antibody. The slides were developed using a diaminobenzidine solution (DAB) as chromagen. The sections were counterstained with hematoxylin, dehydrated in ethanol, and mounted in Permount (Fisher Scientific). Using this method, SIM2 protein was detected in the tumor samples (6/6), but not in the corresponding normal tissues. SIM2 protein was also detected in the early stage colon tumors such as adenomas. Use of anti-SIM2 antibodies in Western blots or ELISAs is specifically envisioned in methods for detecting SIM2 protein in tissue samples as a diagnostic or prognostic assay for SIM2-associated malignancies.

Example 17

Production of a SIM2 Short-Form-Specific Antibody

A preparation including 200 ug of a peptide having the amino acid sequence of SEQ ID NO: 14 emulsified in complete Freund's adjuvant was injected into duplicate rabbits by Sigma Genosys, Tex. Thereafter the rabbits were immunized every two weeks (3×), with 100 ug of the peptide emulsified in incomplete Freund's adjuvant and day 49 bleeds were collected. The rabbits were again immunized with 100 ug of the peptides emulsified in complete Freund's adjuvant every 25 days. Sera from the day 69 and 102 bleeds were analyzed by ELISA, which confirmed that the sera contained antibodies that were reactive to the peptide antigen. The sera from the immunized rabbits, and the preimmune (control) sera were then tested by dot blot analysis using protein lysates from patient-derived colon tumors and RKO cell line lysates. Use of the sera from the immunized rabbits detected the presence of the SIM2 short-form protein in colon tumor samples, whereas the preimmune sera did not. Based on the data from these experiments, appropriate dilutions of the sera (e.g., between 1:200 to 1:2000) were chosen for use with the immunohistochemistry analyses described herein.

Example 18

Protein-Based Diagnostic/Therapeutic Use of SIM2

Antibodies generated against SIM2 proteins can be obtained by immunization of a host animal as described above. Binding of SIM2 proteins by a SIM2-specific antibody is envisioned to inhibit the functional activity of the polypeptide. Because anti-SIM2 antibodies selectively bind cells expressing the SIM2 protein (e.g., cells from colon, pancreas and prostate tumors), they can be used in methods to target an/or destroy such SIM2 expressing cells. For example, SIM2-specific antibodies can be labeled (e.g., radioactively or magnetically) for use in in vivo imaging (e.g., of a human subject's pelvic area for colon cancer diagnoses). As another example, to treat a SIM2 associated cancer, SIM2-specific antibodies can be labeled with a cytotoxic agent (e.g., ricin or $^{125}$I) and administered to an animal having the cancer (e.g., by intratumoral injection). Methods of modifying antibodies that can be internalized by cells are known. For example, an antibody can be conjugated to a ligand whose receptor is found on the cell surface. Upon binding the ligand, the antibody ligand complex can be internalized so that it can enter the cytoplasm.

Example 19

Treatment of Cells With an Antisense Oligonucleotide

RKO colon carcinoma cells were grown in DMEM medium supplemented with 10% fetal bovine serum. Exponentially growing RKO cells were treated with different amounts (e.g., 200–600 nM) of either the antisense (SEQ ID NO: 12) or control reverse antisense (SEQ ID NO: 13) oligonucleotides using Lipofectine (BRL-Life Technologies) as a delivery vehicle and OptiMEM medium according to the manufacturer's instructions. Four hours after the transfection, the cells were washed with phosphate-buffered saline (PBS) and were incubated in DMEM medium supplemented with 10% fetal bovine serum for 24–72 hrs. The cells were monitored for morphological changes by light microscopy. The cells were fixed with methanol in the culture dishes for immunohistochemical analysis, or were removed from the culture dishes by trypsinization and processed for analysis of DNA or RNA. Preliminary analysis indicated that 300 nM was the most effective concentration of the antisense oligonucleotide for inducing a response. Thus, in the experiments described below, unless otherwise indicated, 300 nM of antisense oligonucleotides was used. Other cells lines such as MDA breast carcinoma cells (which does not express the SIM2 short-form) were used as an additional control in various experiments described herein to demonstrate the specificity of effects of the antisense oligonucleotide.

Example 20

Measurement of Apoptosis

Cells undergoing programmed cell death (apoptosis) in response to treatment demonstrate diverse changes which can be easily measured. For example, one of the hallmarks of apoptosis is DNA fragmentation (See, e.g., Apoptosis. Afford, S. and Randhawa S., Mol. Pathol. 53(2): 55–63, 2000; and Apoptosis in Cancer: Cause and Cure. Kaufmann, S. H., and Gores, G. J.: Bioessays 22(11): 1007–17, 2000). Fragmentation of genomic DNA from cells undergoing apoptosis can be measured by detecting the presence of ladders of oligosomes after agarose gel electrophoresis. To analyze apoptosis, genomic DNA from RKO colon cancer cells treated with either the antisense oligonucleotide (SEQ ID NO: 12) or the control reverse antisense oligonucleotide (SEQ ID NO: 13) was isolated using the DNAzol kit (BRL-Life technologies). The isolated DNA was then separated on a 1% agarose gel. The separated products on the gel were then transferred to a nitrocellulose membrane. The membrane was hybridized with a $^{32}$p labeled genomic DNA probe derived from the parent RKO colon cancer cells. The hybridized blots were then washed at high stringency (0.1× SSC, 0.1% SDS) at 68° C. and autoradiographed. The results showed that the cells treated with the antisense oligonucleotide exhibited significantly more DNA fragmentation (as determined by ladder formation) than did cells treated with the control oligonucleotide.

In other experiments, apoptosis was analyzed using the Apotag (TUNNEL assay) detection system kit (Intergen Company, NY). This kit allows DNA fragmentation inside a single cell to be measured by utilizing terminal deoxytransferase (TdT) to label the 3' hydroxy termini generated during DNA fragmentation with modified nucleotides (digoxigenin-dNTP). An anti-digoxigenin antibody conjugated with peroxidase is then used to detect the cells containing the fragmented DNA by using a peroxidase substrate under a microscope. See, Gold, R., Lab. Inves. 71:219–222, 1994). In these experiments, RKO cells treated with the antisense oligonucleotide exhibited significantly more DNA fragmentation (as determined the Apotag method) than did cells treated with the control oligonucleotide.

Example 21

Immunohistochemical Analysis of Bcl-2

An immunohistochemical analysis of Bcl-2 expression was undertaken in the antisense-treated colon cancer cells. RKO colon cancer cells were treated as described above with 300 nM of either antisense (SEQ ID NO: 12) or the control reverse antisense (SEQ ID NO: 13) for 72 hrs and the cells were analyzed by immunohistochemistry using polyclonal antibodies to bcl-2 (Santacruz Biotechnology). Immunohistochemical detection of bcl-2 was performed as described in Scheurle et al., Anticancer. Res. 20:2091–2096, 2000 by incubating the treated RKO cells with the primary anti-bcl-2 antibody. Bound primary antibody was detected by staining the cells with a horseradish peroxidase-labeled dextran polymer conjugated affinity-purified goat anti-rabbit immunoglobulin secondary antibody. The slides were developed using a diaminobenzidine solution (DAB) as chromagen. The cells were counterstained with hematoxylin, dehydrated in ethanol, and mounted in Permount (Fisher Scientific). The results indicated that bcl-2 protein levels were decreased in the antisense-treated cells compared to the control reverse antisense-treated cells, a finding consistent with the notion that the antisense-treatment induces apoptosis in the RKO cells. In other experiments (not shown), Bcl-2 mRNA levels were decreased in the antisense-treated cells compared to the control reverse antisense-treated cells.

Example 22

Diagnostic Use of SIM2 Short-Form Specific Antibody in Prostate Tumors

Biopsy-derived prostate tumor and normal tissues obtained from a single patient were prepared as paraffin sections and analyzed by immunohistochemistry as described in Example 16 (above) using the polyclonal antibody against the peptide of SEQ ID NO: 14 described in Example 17 above. The results showed that the expression of SIM2 short-form was detected in the tumor, but not in the normal tissue. In similar experiments, referring to Table 1 (below), the SIM-2 short-form was detected in a section of Benign Prostatic Hyperplasia and in a section of prostate cancer, but not in the matched normal prostatic tissue. None of the normal prostate tissues (6/6) examined by immunohistochemistry stained positive for the presence of the SIM2 short-form. Similarly, stromal hyperplasia (which typically does not progress to prostate cancer) samples were largely negative (15/18). All samples taken from patients with both BPH and Prostate Interstitial Neoplasia (PIN) showed positive staining (6/6). Additionally, all samples of prostate cancer regardless of stage (Gleeson grades I–IV were examined) showed positive staining for SIM2 short-form.

TABLE 1

Summary of IHC results from colon, prostate, and pancreas tissues.

| Nature of tissues | Results* |
|---|---|
| Colon | |
| Normal | 5/5 (Negative) |
| Adenomas | 3/3 (Positive) |
| Tumors | 6/6 (Positive) |
| Prostate | |
| Normal | 6/6 (Negative) |
| Stromal hyperplasia | 15/18 (Negative) |
| BPH | 12/22 (Negative)* * |
| BPH + PIN | 6/6 (Positive) |
| BPH matched with cancer | 9/9 (Positive) |
| Tumors(GL. I–IV) | 12/12 (Positive) |
| Pancreas | |
| Normal | 6/6 (Negative) |
| Adenomas | 2/2 (Positive) |
| Carcinomas | 6/6 (Positive) |

Indicated types of tissues were analyzed by immunohistochemistry using an antibody raised against the peptide shown in SEQ ID NO: 14 and the staining for SIM2 short-form was scored which varied from + to +++.
*Scoring was performed by light microscopic analysis of at least 500 cells covering at least 75% of the sections. Negative = No cells stained for SIM2 short-form; Positive-Level varies from + to +++; + = 10–25% cells stained for SIM2 short-form; ++ = 25–50% cells stained for SIM2 short-form; and +++ = 50–75% of cells stained for SIM2 short-form.
* *Remaining 10 BPH are clear positives (+ to ++). Recent samples and no cancer for these patients was observed at time of analysis.

Example 23

Diagnostic Use of SIM2 Short-Form Specific Antibodies in Colon Tumor

Biopsy-derived colon tumor and normal tissues obtained from a single patient were prepared as paraffin sections and analyzed by immunohistochemistry as described in Example 16 using the polyclonal antibody against the peptide of SEQ ID NO: 13 described in Example 17 above. In these experiments, the expression of SIM2 short-form in a matched set of colon tissue samples (normal=CN-15; tumor=CT15) was analyzed by immunohistochemistry. Expression of SIM2 short-form was detected in both tumor sections, but not in either of the normal tissue sections. In other experiments, referring to Table 1, 3 of 3 early stage colon cancers including adenomas stained positive for SIM2 short-form. In contrast, 5 of 5 of the normal colon tissue samples tested were negative for the SIM2 short-form. All the tumors (6/6) examined showed positive staining for SIM2 short-form. Thus, colon cells from patients which are obtained during routine colonoscopy can be monitored for SIM2 short-form in a method for diagnosing colon cancer. In addition, since colon cells are shed in the feces, it will likely be possible to detect early stages of colon cancers by analyzing the fecal material for the presence of SIM2 short-form.

Example 24

Diagnostic Use of SIM2 Short-Form Specific Antibodies in Pancreas Tumors

Biopsy-derived colon tumor and normal tissues obtained from a single patient were prepared as paraffin sections and analyzed by immunohistochemistry as described in Example 16 using the polyclonal antibody against the peptide of SEQ ID NO: 14 described in Example 17. In these experiments, SIM2 short-form expression was examined in two matched sets of pancreas tumors. SIM2 short-form was detected in the sections of tumor, but not in the normal tissue sections. In addition, referring to Table 1, diverse normal pancreas tissues (6/6) were negative for SIM2 short-form expression, while both advanced tumors (6/6) as well as adenomas (early stage tumors) showed positive SIM2 short-form staining (2/2). Thus, the SIM2 short-form can be used as a marker for pancreatic cancer. And since pancreatic cancer cells are shed in the feces, it possible that this method of detection can be used with fecal-derived material as well.

Example 25

Detection of Metastasis in Colon, Pancreas and Prostate Tumor Patients

Expression of SIM2 short-form protein has not been detected in bone marrow cells or peripheral blood lymphocytes. Since metastasizing cancer cells often migrate via the blood or lymphatic circulation, the identification of metastasis by monitoring these tissues for the expression of the SIM2 short-form is specifically envisioned.

Example 26

Monitoring Response to Therapy

Patients treated with drugs or surgery for colon, pancreas, or prostate cancers can be monitored for recurrence of the cancers by measuring SIM2 short-form expression in materials such as blood, bone marrow, or feces. Presence of the SIM2 short-form in these materials would indicate that the tumor had recurred.

Example 27

Therapeutic Use of SIM2 Short-Form: Antisense Inhibition

Colon carcinoma cells (RKO cells) were treated with either the antisense oligonucleotide of SEQ ID NO: 12, the control reverse antisense oligonucleotide of SEQ ID NO: 13, or the vehicle (saline) for 72 hours, and their growth rate was assessed. Growth was assessed every 24 hrs by microscopy wherein the cell viability density in cultures treated with the antisense or control oligonucleotide was assessed using trypan blue dye exclusion and a hemocytometer. The microscopic analysis revealed that the antisense-treated cells exhibited an increased amount of cytoplasm and decreased nuclear integrity compared to the control cells. The growth of the antisense-treated cells was significantly inhibited in comparison to either of the controls. The antisense-treated cells also showed various hallmarks of cells undergoing programmed cell death (apoptosis) including cell-shrinkage, increased cytoplasm, and disappearance of the nuclear membrane. Since induction of apoptosis in cancer cells is a way to kill the cancer, a therapeutic use of an antisense oligonucleotide (e.g., the antisense oligonucleotide of SEQ ID NO: 12) to kill cancer cells is envisioned.

In other experiments, antisense-treated RKO colon carcinoma cells showed reduced levels of SIM2 short-form mRNA as measured by RT-PCR. RKO colon carcinoma cells were treated with 300 nM of either the antisense (SEQ ID NO: 12) or the reverse antisense (SEQ ID NO: 13) for 72 hrs. Total RNA from these cells was isolated and reverse transcribed, and the cDNAs were analyzed by PCR using SIM2 short-form specific PCR primers as shown in SEQ ID NO: 15 (sense) and SEQ ID NO: 16 (antisense). This primer pair defines an amplicon of a 619 bp product unique to the short-form. C-15=SIM2 short-form and actin=house keeping gene control. Negative=template minus PCR control.

In the same cells, more genomic DNA was broken down into oligosomes (ladder formation) in the antisense oligonucleotide-treated cells compared to the control reverse antisense oligonucleotide-treated cells as measured by a Southern blot analysis of the DNA followed by hybridization to total genomic DNA from the untreated RKO cells. These results indicate that the antisense (SEQ ID NO: 12) kills the cancer cells by a specific inhibition of the target protein, and that this inhibition results induces apoptosis.

In other experiments, induction of apotosis in antisense-treated cells was analyzed by monitoring DNA laddering within the treated cells in situ using the Apotag kit (Intergrin Company, NY) to measure the nicked DNA within the cells. The RKO cells treated with either the antisense oligonucleotide of SEQ ID NO: 12 or the control reverse antisense oligonucleotide of SEQ ID NO: 13. The antisense-treated cells stained much more intensely than the control reverse antisense-treated cells indicating that apoptosis was initiated in the former.

Expression of the bcl-2 gene occurs in diverse tumors and has been implicated as being an inhibitor of apoptosis in the tumor cells. If a cell undergoes apoptosis occurs, the level of bcl-2 protein expressed by the cell should be reduced. RKO colon cancer cells were treated with 300 nM of either antisense (SEQ ID NO: 12) or the control reverse antisense (SEQ ID NO: 13) for 72 hrs and the cells were analyzed by immunohistochemistry using polyclonal antibodies to bcl-2 (Santacruz Biotechnology). The results showed that the antisense-treated cells expressed much lower levels of bcl-2 than did the control reverse antisense-treated cells. In other experiments using the same cells, the levels of bcl-2 mRNA were reduced in the antisense-treated cells as compared to the control reverse antisense-treated cells.

To further investigate possible toxicity caused by inhibition of SIM2 short form expression or antisense oligonucleotide treatment, a breast cancer cell line (MDA-231, available from the ATCC) that does not express SIM2 short-form treated with 300 nM of either antisense (SEQ ID NO: 12) or the control reverse antisense (SEQ ID NO: 13) for 72 hrs. In neither case was any inhibition of growth seen. In other experiments, DNA from these cells did not show the laddering indicative of apoptosis. In addition, primary human normal cells such as prostate epithelial cells or the renal proximal epithelial cells (Clonetics) did not show growth inhibition when treated with the same antisense for 72 hrs nor any evidence of DNA laddering.

Example 28

Treatment of Animals With SIM-2 Antisense Oligonucleotides

Non-irradiated Ncr nu/nu mice (5–6 weeks old, 22–24 g body weight) were injected subcutaneously with $1 \times 10^6$ RKO colon carcinoma cells. Beginning twenty-four hours later, vehicle (PBS, control), EZ-1 (antisense; SEQ ID NO: 12) or EZ-3 (reverse antisense; SEQ ID NO: 13) were injected (N=6/set) at 1 mg/kg, subcutaneously on the contralateral side, twice weekly. These oligonucleotides were synthesized as a second generation oligonucleotides (i.e., with a phosphorothioate-2 O methyl chimeric backbone) by Oligos etc. Wilsonville, Oreg., 97070) and purified by HPLC. The oligonucleotides were prepared in phosphate-buffered saline (vehicle) at 10 mg/ml (stock) before injection. The mice were treated with either the vehicle (PBS), EZ-1 or EZ-3 at 10 mg/kg dose subcuteneously twice weekly for 28 days and the tumor size and mean body weight measured. This treatment was continued for 21 days. As shown in FIG. 1, the tumor volume in each animal was measured at various time points. The left side graph shows mean body weight as a measure of gross toxicity and the right side graph shows efficacy of the treatment. The group treated with EZ-1 (antisense; SEQ ID NO: 12) showed much slower tumor growth than the control groups.

Other Embodiments

This description has been by way of example of how the compositions and methods of invention can be made and carried out. Those of ordinary skill in the art will recognize that various details may be modified in arriving at the other detailed embodiments, and that many of these embodiments will come within the scope of the invention.

Therefore, to apprise the public of the scope of the invention and the embodiments covered by the invention, the following claims are made.

What is claimed is:

1. A method of decreasing SIM2 short form gene expression comprising the steps of:
   (a) providing a cell that expresses a SIM2 short form nucleic acid having the sequence of SEQ ID NO:2; and
   (b) introducing into the cell an agent that decreases the expression of a nucleic acid having the sequence of SEQ ID NO: 2 or the complement of SEQ ID NO: 2 in the cell, wherein the agent is an oligonucleotide that hybridizes under stringent conditions to a nucleic acid having the sequence of SEQ ID NO: 2 or the complement of SEQ ID NO: 2, said oligonucleotide being selected from the group consisting of an antisense oligonucleotide, a ribozyme, and a triple-helix forming molecule.

2. The method of claim 1, wherein the agent is an antisense oligonucleotide that hybridizes under stringent hybridization conditions to a nucleic acid having a sequence that is a complement of the nucleic acid having the sequence of SEQ ID NO:2.

3. The method of claim wherein the antisense oligonucleotide less than about 100 nucleotides in length.

4. A method of decreasing SIM2 short form gene expression comprising the steps of:
   (a) providing a cell that expresses a SIM2 short form nucleic acid having the sequence of SEQ ID NO:2; and
   (b) introducing into the cell an agent that decreases the expression of a nucleic acid having the sequence of the complement of SEQ ID NO:2 in the cell, wherein the agent is an antisense oligonucleotide that hybridizes under stringent hybridization conditions to said sequence that is the complement of a nucleic acid having the sequence of SEQ ID NO:2, said antisense oligonucleotide being at least 18 nucleotides in length and comprising the nucleic acid sequence identified as SEQ ID NO:12.

5. The method of claim 1, wherein said oligonucleotide is a ribozyme.

6. The method of claim 1, wherein said oligonucleotide is a triple helix forming molecule that hybridizes under stringent conditions to a promoter region of a nucleic acid having SEQ ID NO:2.

7. The method of claim 3, wherein the antisense oligonucleotide hybridizes under stringent conditions to a polynucleotide sequence in the 5' untranslated, 3' untranslated, or coding region of said nucleic acid that is the complement of SEQ ID NO:2.

8. The method of claim 7, wherein the antisense oligonucleotide hybridizes under stringent conditions to a polynucleotide sequence that is between the −10 and +10 positions of said nucleic acid.

9. The method of claim 7, wherein the antisense oligonucleotide hybridizes under stringent conditions to a ploynucleotide sequence that is in the 3' untranslated region of said nucleic acid.

10. The method of claim 4, wherein the antisense oligonucleotide comprises at least one modified phosphate backbone.

11. The method of claim 10, wherein the modified phosphate backbone is selected from the group consisting of a phosphorothioate, a phosphorodithioate, a phosphoramidothioate, a phosphoramidate, a phosphordiamidate, a methylphosphonate, an alkyl phosphotriester, or a formacetal.

12. The method of claim 4, wherein the antisense oligonucleotide comprises at least one modified sugar moiety.

13. The method of claim 12, wherein the modified sugar moiety is selected from the group consisting of arabinose, 2-fluoroarabinose, xylulose, and hexose.

14. The method of claim 4, wherein the antisense oligonucleotide comprises at least one modified base.

15. The method of claim 14, wherein said oligonucleotide is a 2'-O-methylribonucleotide.

16. The method of claim 14, wherein said oligonucleotide is a chimeric RNA-DNA analog.

* * * * *

SEQUENCE LISTING

<160> NUMBER OF SEQ ID NOS: 16

<210> SEQ ID NO 1
<211> LENGTH: 3920
<212> TYPE: DNA
<213> ORGANISM: Homo sapiens

<400> SEQUENCE: 1
actcactata gggctcgagc ggccgcccgg gcaggtgggg ctccgcgggc ctggagcacg    60
gccgggtcta atatgcccgg agccgaggcg cgatgaagga gaagtccaag aatgcggcca   120
agaccaggag ggagaaggaa aatggcgagt tttacgagct tgccaagctg ctcccgctgc   180
cgtcggccat cacttcgcag ctggacaaag cgtccatcat ccgcctcacc acgagctacc   240
tgaagatgcg cgccgtcttc cccgaaggtt taggagacgc gtggggacag ccgagccgcg   300

-continued

| | |
|---|---|
| ccgggcccct ggacggcgtc gccaaggagc tgggatcgca cttgctgcag actttggatg | 360 |
| gatttgtttt tgtggtagca tctgatggca aaatcatgta tatatccgag accgcttctg | 420 |
| tccatttagg cttatcccag gtggagctca cgggcaacag tatttatgaa tacatccatc | 480 |
| cttctgacca cgatgagatg accgctgtcc tcacggccca ccagccgctg caccaccacc | 540 |
| tgctccaaga gtatgagata gagaggtcgt tctttcttcg aatgaaatgt gtcttggcga | 600 |
| aaaggaacgc gggcctgacc tgcagcggat acaaggtcat ccactgcagt ggctacttga | 660 |
| agatcaggca gtatatgctg gacatgtccc tgtacgactc ctgctaccag attgtgggc | 720 |
| tggtggccgt gggccagtcg ctgccaccca gtgccatcac cgagatcaag ctgtacagta | 780 |
| acatgttcat gttcagggcc agccttgacc tgaagctgat attcctggat tccagggtga | 840 |
| ccgaggtgac gggttacgag ccgcaggacc tgatcgagaa gaccctatac catcacgtgc | 900 |
| acggctgcga cgtgttccac ctccgctacg cacaccacct cctgttggtg aagggccagg | 960 |
| tcaccaccaa gtactaccgg ctgctgtcca agcggggcgg ctgggtgtgg gtgcagagct | 1020 |
| acgccaccgt ggtgcacaac agccgctcgt cccggcccca ctgcatcgtg agtgtcaatt | 1080 |
| atgtactcac ggagattgaa tacaaggaac ttcagctgtc cctggagcag gtgtccactg | 1140 |
| ccaagtccca ggactcctgg aggaccgcct tgtctacctc acaagaaact aggaaattag | 1200 |
| tgaaacccaa aaataccaag atgaagacaa agctgagaac aaacccttac cccccacagc | 1260 |
| aatacagctc gttccaaatg gacaaactgg aatgcggcca gctcggaaac tggagagcca | 1320 |
| gtcccctgc aagcgctgct gctcctccag aactgcagcc ccactcagaa agcagtgacc | 1380 |
| ttctgtacac gccatcctac agcctgccct tctcctacca ttacggacac ttccctctgg | 1440 |
| actctcacgt cttcagcagc aaaaagccaa tgttgccggc caagttcggg cagccccaag | 1500 |
| gatcccttg tgaggtggca cgcttttttcc tgagcacact gccagccagc ggtgaatgcc | 1560 |
| agtggcatta tgccaacccc ctagtgccta gcagctcgtc tccagctaaa atcctccag | 1620 |
| agccaccggc gaacactgct aggcacagcc tggtgccaag ctacgaagcg cccgccgccg | 1680 |
| ccgtgcgcag gttcggcgag gacaccgcgc ccccgagctt cccgagctgc ggccactacc | 1740 |
| gcgaggagcc cgcgctgggc ccggccaaag ccgcccgcca ggccgcccgg gacggggcgc | 1800 |
| ggctggcgct ggcccgcgcg gcacccgagt gctgcgcgcc cccgacccc gaggcccgg | 1860 |
| gcgcgccggc gcagctgccc ttcgtgctgc tcaactacca ccgcgtgctg gcccggcgcg | 1920 |
| gaccgctggg gggcgccgca cccgccgcct cggcctggc ctgcgctccc ggcggccccg | 1980 |
| aggcggcgac cggcgcgctg cggctccggc acccgagccc cgccgccacc tccccgcccg | 2040 |
| gcgcgccct gccgcactac ctgggcgcct cggtcatcat caccaacggg aggtgacccg | 2100 |
| ctggccgccc gcgccaggag cctggacccg gcctcccggg gctgcggcgc caccgagccc | 2160 |
| ggcaaatgcg cacgacctac attaatttat gcagagacag ctgtttgaat tggaccccgc | 2220 |
| cgccgacttg cggatttcca ccgcggaggc cccgcgcgcc ggtgccgagg ccgaggagc | 2280 |
| gcccgggtcc gggcaggtga ccgcccgcct ctgtcctgcg agggccggtg cgacccagtt | 2340 |
| gctgggggct tggtttcctc accttgaaat cgggcttcac gcgtcttgcc ttgtcccaa | 2400 |
| cgttccacaa cagtcccgct gggggattga agcggtttca ctccgcaaat atcctccact | 2460 |
| ttcaggaggg aaaacccacc ctaccacagt ccgctcttcc aagtggacgg cagacctggg | 2520 |
| aggggacgcc tgtgtcacga gcccttttag atgcttaggt gaaggcagaa gtgatgattg | 2580 |
| taagtcccat gaatacacaa ctccactgtc tttaaaagtc attcaagagt ctcattattt | 2640 |

-continued

```
ttgttttat     ttaaccctt     cttcaataca    aaaagccaac    aaaccaagac    taaggggtg     2700 accatgcaat    tccattttgt    gtctgtgaac    ataggtgtgc    ttcccaaata    cattaacaag    2760
ctcttacttc    cccctaaccc    ctatgaactc    ttgataacac    caagagtagc    accttcagaa    2820
tatattgaat    aggcattaaa    tgcaaaaata    tatatgtagc    cagacagttt    atgagaatga    2880
ccctgtcaag    cttcattatt    acgtggcaaa    atccctctgg    cccacacaga    tctgtaattc    2940
actaggctcg    tgtttgctac    aaatagtgct    aataaagtta    aattgcacgt    gcaatacgga    3000
acactgtcaa    tggactgcac    cttgtgaagg    aaaaacatgc    ttaaggggt     gtaatgaaaa    3060 tgatgtagac    atttaagca     ttttctacac    agcgagaaaa    cttcgtaaga    acatgttacg    3120
tgtgcaacag    gtaaacagaa    atcctttcat    aaagcaccag    cagtgttaa     aaaatgagct    3180 tccattaatt    tttactttt     atgggttttg    cttaaagatc    tcaacatgga    aaaatcctgt    3240
catggctctg    aactgcacaa    tgcattgaac    cgccgtcctt    caattttctt    cacactatca    3300
acactgcagc    attttgctgc    tttatcaaaa    tggtttattt    taggaaactt    ttccaccctt    3360
tctgaatgga    agaggtttt     cacaaatgtt    ttaaactcat    cgttctaaaa    tcaagtgcac    3420
ctacaccaac    tgctctcaaa    atgtgaactg    actttttttt    ttttttttt     gccaaccctg    3480 tgtcacttag    tgaggacctg    acacaatccc    tacagggtgt    ctgtcagtgg    gcctcatggt    3540
aagagtcaca    atttgcaaat    ttaggaccgt    gggtcatgca    gcgaagggc     tggatggtag    3600 gaagggatgt    gcccgcctct    ccacgcactc    agctatacct    cattcacagc    tccttgtgag    3660
tgtgtgcaca    ggaaataagc    cgagggtatt    atttttttat    gttcatgagt    cttgtaatta    3720
aaccgtgatt    cttgaaaggt    gtaggtttga    ttactaggag    ataccaccga    cattttcaa     3780 taaagtactg    caaaatgctt    ttgtgtctac    cttgttatta    acttttgggg    ctgtatttag    3840
taaaaataaa    tcaaggctat    cggagcagtt    caataacaaa    ggttactgtt    gagaaaaaag    3900
accctatcat    agatttacaa                                                            3920
```

<210> SEQ ID NO 2
<211> LENGTH: 2859
<212> TYPE: DNA
<213> ORGANISM: Homo sapiens

<400> SEQUENCE: 2

```
actcactata    gggctcgagc    ggccgcccgg    gcaggtgggg    ctccgcgggc    ctggagcacg     60
gccgggtcta    atatgcccgg    agccgaggcg    cgatgaagga    gaagtccaag    aatgcggcca    120
agaccaggag    ggagaaggaa    aatggcgagt    tttacgagct    tgccaagctg    ctcccgctgc    180
cgtcggccat    cacttcgcag    ctggacaaag    cgtccatcat    ccgcctcacc    acgagctacc    240
tgaagatgcg    cgccgtcttc    cccgaaggtt    taggagacgc    gtggggacag    ccgagccgcg    300
ccgggcccct    ggacggcgtc    gccaaggagc    tgggatcgca    cttgctgcag    actttggatg    360
gatttgtttt    tgtggtagca    tctgatggca    aaatcatgta    tatatccgag    accgcttctg    420 tccattagg     cttatcccag    gtggagctca    cgggcaacag    tatttatgaa    tacatccatc    480
cttctgacca    cgatgagatg    accgctgtcc    tcacggccca    ccagccgctg    caccaccacc    540
tgctccaaga    gtatgagata    gagaggtcgt    tctttcttcg    aatgaaatgt    gtcttggcga    600
aaaggaacgc    gggcctgacc    tgcagcggat    acaaggtcat    ccactgcagt    ggctacttga    660
agatcaggca    gtatatgctg    acatgtccc    tgtacgactc    ctgctaccag    attgtgggc     720 tggtggccgt    gggccagtcg    ctgccaccca    gtgccatcac    cgagatcaag    ctgtacagta    780
acatgttcat    gttcagggcc    agccttgacc    tgaagctgat    attcctggat    tccagggtga    840
```

-continued

```
ccgaggtgac gggttacgag ccgcaggacc tgatcgagaa gaccctatac catcacgtgc      900
acggctgcga cgtgttccac ctccgctacg cacaccacct cctgttggtg aagggccagg      960
tcaccaccaa gtactaccgg ctgctgtcca agcggggcgg ctgggtgtgg gtgcagagct     1020
acgccaccgt ggtgcacaac agccgctcgt cccggcccca ctgcatcgtg agtgtcaatt     1080
atgtactcac ggagattgaa tacaaggaac ttcagctgtc cctggagcag gtgtccactg     1140
ccaagtccca ggactcctgg aggaccgcct tgtctacctc acaagaaact aggaaattag     1200
tgaaacccaa aaataccaag atgaagacaa agctgagaac aaacccttac cccccacagc     1260
aatacagctc attccaaatg gacaaactgg aatgcggcca gctcggaaac tggagagcca     1320
gtcccctgc aagcgctgct gctcctccag aactgcagcc ccactcagaa agcagtgacc      1380
ttctgtacac gccatcctac agcctgccct tctcctacca ttatggacac ttccctctgg     1440
actctcactt cttcagcagc aaaaagccaa tgttgccggc caagttcggg cagccccaag     1500
gatcccttg tgaggtggca cgcttttttcc tgagcacaat gccagccagc ggtgaatgcc     1560
agtggcatta tgccaacccc ctagtgccta gcagctcgtc tccagctaaa atcctccag     1620
agccaccggc gaacactgct aggcacagcc tggtgccaag ctacgaaggt gggtcaggtc     1680
tgctcgtggg gaaggtggga ggactgcgca cggccgggag ccgaagcagc catggcggtg     1740
ggtggcagat ggagacagaa ccctcacgct ttgggcaaac ttgccctctt tctgcttcta     1800
agtagggctt gctgtgcttt cttgctctca atgcaggtgc tcctcgagag tgagaaatgg     1860
cagtctgcct gcctcgggga cactagtgac agtataaagg gcaaaggaaa accgagtatc     1920
tggccttcac gtaaatcctg gccacattca ccaaccaaag ggggacagtg attttcaaaa     1980
ccagctccca tgtgctgaga cacccccagc tgcatttctt ttgcaagatt cctttccact     2040
ccaaccagaa gtgaatattt gagacaaacg gcctattggc tattttccca tgccagtttt     2100
ggaagtgggg aaaactatgg tggaaatttg tgggcttggg gacagaaatg ccactccacca    2160
acccagggca agaacacaa accctccagg cctcagtttc ttcacctgta aaatggggtg      2220
aagctgtgat gtgcctactc ccaaggacac gacacacagt agggacctgc cctgtacatg     2280
ctagttcaac agaaaggaat ggcctttcac cttctcctgg tggcaggcaa gcagatgtcc     2340
tctgcggaga taccgccagc tccccaggac gcagactgac tcctgtttgc tcgctggacc     2400
aaccccaggc agaaggtgga aggtgggaac agaggtttag ctgcaggaca tgtattccca     2460
ttgcaccgag acctaactgc cgctcagagt gtagaccgag atggtgcaga tgcctgcagt     2520
gccattaaaa tgtgggtgaa ggtgacatca ggattatgtg ccccaggccg ggctcagtgg     2580
ctcacacctg taatcccagc actttgggag gccaaggtgg gcggatcacc tgaggtcagg     2640
agtttgcgac aagcctgcca acaagctgaa accccatctc cactaaaaat acaaaaatta     2700
gttgggcatg gtggtgagca cctgtaatcc cagctactct ggaggctgag ataggaggat     2760
cacttgaacc cgggaggtgg aggttgcagt gagctaagat cacatcactg cactccagcc     2820
tgggtaacag agtgagactg tctcaaaaaa aaaaaaaaa                            2859
```

<210> SEQ ID NO 3
<211> LENGTH: 667
<212> TYPE: PRT
<213> ORGANISM: Homo sapiens

<400> SEQUENCE: 3

```
Met Lys Glu Lys Ser Lys Asn Ala Ala Lys Thr Arg Arg Glu Lys Glu
1               5                   10                  15
```

```
Asn Gly Glu Phe Tyr Glu Leu Ala Lys Leu Leu Pro Leu Pro Ser Ala
            20                  25                  30
Ile Thr Ser Gln Leu Asp Lys Ala Ser Ile Ile Arg Leu Thr Thr Ser
            35                  40                  45
Tyr Leu Lys Met Arg Ala Val Phe Pro Glu Gly Leu Gly Asp Ala Trp
 50                  55                  60
Gly Gln Pro Ser Arg Ala Gly Pro Leu Asp Gly Val Ala Lys Glu Leu
 65              70                  75                  80
Gly Ser His Leu Leu Gln Thr Leu Asp Gly Phe Val Phe Val Val Ala
                85                  90                  95
Ser Asp Gly Lys Ile Met Tyr Ile Ser Glu Thr Ala Ser Val His Leu
            100                 105                 110
Gly Leu Ser Gln Val Glu Leu Thr Gly Asn Ser Ile Tyr Glu Tyr Ile
            115                 120                 125
His Pro Ser Asp His Asp Glu Met Thr Ala Val Leu Thr Ala His Gln
            130                 135                 140
Pro Leu His His His Leu Leu Gln Glu Tyr Glu Ile Glu Arg Ser Phe
145                 150                 155                 160
Phe Leu Arg Met Lys Cys Val Leu Ala Lys Arg Asn Ala Gly Leu Thr
                165                 170                 175
Cys Ser Gly Tyr Lys Val Ile His Cys Ser Gly Tyr Leu Lys Ile Arg
            180                 185                 190
Gln Tyr Met Leu Asp Met Ser Leu Tyr Asp Ser Cys Tyr Gln Ile Val
            195                 200                 205
Gly Leu Val Ala Val Gly Gln Ser Leu Pro Pro Ser Ala Ile Thr Glu
 210                 215                 220
Ile Lys Leu Tyr Ser Asn Met Phe Met Phe Arg Ala Ser Leu Asp Leu
225                 230                 235                 240
Lys Leu Ile Phe Leu Asp Ser Arg Val Thr Glu Val Thr Gly Tyr Glu
                245                 250                 255
Pro Gln Asp Leu Ile Glu Lys Thr Leu Tyr His His Val His Gly Cys
            260                 265                 270
Asp Val Phe His Leu Arg Tyr Ala His His Leu Leu Leu Val Lys Gly
            275                 280                 285
Gln Val Thr Thr Lys Tyr Tyr Arg Leu Leu Ser Lys Arg Gly Gly Trp
            290                 295                 300
Val Trp Val Gln Ser Tyr Ala Thr Val Val His Asn Ser Arg Ser Ser
305                 310                 315                 320
Arg Pro His Cys Ile Val Ser Val Asn Tyr Val Leu Thr Glu Ile Glu
                325                 330                 335
Tyr Lys Glu Leu Gln Leu Ser Leu Glu Gln Val Ser Thr Ala Lys Ser
            340                 345                 350
Gln Asp Ser Trp Arg Thr Ala Leu Ser Thr Ser Gln Glu Thr Arg Lys
            355                 360                 365
Leu Val Lys Pro Lys Asn Thr Lys Met Lys Thr Lys Leu Arg Thr Asn
 370                 375                 380
Pro Tyr Pro Pro Gln Gln Tyr Ser Ser Phe Gln Met Asp Lys Leu Glu
385                 390                 395                 400
Cys Gly Gln Leu Gly Asn Trp Arg Ala Ser Pro Ala Ser Ala Ala
                405                 410                 415
Ala Pro Pro Glu Leu Gln Pro His Ser Glu Ser Ser Asp Leu Leu Tyr
            420                 425                 430
```

-continued

```
Thr Pro Ser Tyr Ser Leu Pro Phe Ser Tyr His Tyr Gly His Phe Pro
        435                 440                 445

Leu Asp Ser His Val Phe Ser Lys Lys Pro Met Leu Pro Ala Lys
    450                 455                 460

Phe Gly Gln Pro Gln Gly Ser Pro Cys Glu Val Ala Arg Phe Phe Leu
465                 470                 475                 480

Ser Thr Leu Pro Ala Ser Gly Glu Cys Gln Trp His Tyr Ala Asn Pro
                485                 490                 495

Leu Val Pro Ser Ser Ser Pro Ala Lys Asn Pro Glu Pro Pro
            500                 505                 510

Ala Asn Thr Ala Arg His Ser Leu Val Pro Ser Tyr Glu Ala Pro Ala
        515                 520                 525

Ala Ala Val Arg Arg Phe Gly Glu Asp Thr Ala Pro Pro Ser Phe Pro
530                 535                 540

Ser Cys Gly His Tyr Arg Glu Glu Pro Ala Leu Gly Pro Ala Lys Ala
545                 550                 555                 560

Ala Arg Gln Ala Ala Arg Asp Gly Ala Arg Leu Ala Leu Ala Arg Ala
                565                 570                 575

Ala Pro Glu Cys Cys Ala Pro Pro Thr Pro Glu Ala Pro Gly Ala Pro
            580                 585                 590

Ala Gln Leu Pro Phe Val Leu Leu Asn Tyr His Arg Val Leu Ala Arg
        595                 600                 605

Arg Gly Pro Leu Gly Gly Ala Ala Pro Ala Ala Ser Gly Leu Ala Cys
        610                 615                 620

Ala Pro Gly Gly Pro Glu Ala Ala Thr Gly Ala Leu Arg Leu Arg His
625                 630                 635                 640

Pro Ser Pro Ala Ala Thr Ser Pro Pro Gly Ala Pro Leu Pro His Tyr
                645                 650                 655

Leu Gly Ala Ser Val Ile Ile Thr Asn Gly Arg
            660                 665

<210> SEQ ID NO 4
<211> LENGTH: 570
<212> TYPE: PRT
<213> ORGANISM: Homo sapiens

<400> SEQUENCE: 4

Met Lys Glu Lys Ser Lys Asn Ala Ala Lys Thr Arg Arg Glu Lys Glu
1               5                   10                  15

Asn Gly Glu Phe Tyr Glu Leu Ala Lys Leu Leu Pro Leu Pro Ser Ala
            20                  25                  30

Ile Thr Ser Gln Leu Asp Lys Ala Ser Ile Ile Arg Leu Thr Thr Ser
        35                  40                  45

Tyr Leu Lys Met Arg Ala Val Phe Pro Glu Gly Leu Gly Asp Ala Trp
    50                  55                  60

Gly Gln Pro Ser Arg Ala Gly Pro Leu Asp Gly Val Ala Lys Glu Leu
65                  70                  75                  80

Gly Ser His Leu Leu Gln Thr Leu Asp Gly Phe Val Phe Val Val Ala
                85                  90                  95

Ser Asp Gly Lys Ile Met Tyr Ile Ser Glu Thr Ala Ser Val His Leu
            100                 105                 110

Gly Leu Ser Gln Val Glu Leu Thr Gly Asn Ser Ile Tyr Glu Tyr Ile
        115                 120                 125

His Pro Ser Asp His Asp Glu Met Thr Ala Val Leu Thr Ala His Gln
    130                 135                 140
```

-continued

```
Pro Leu His His His Leu Leu Gln Glu Tyr Glu Ile Glu Arg Ser Phe
145                 150                 155                 160

Phe Leu Arg Met Lys Cys Val Leu Ala Lys Arg Asn Ala Gly Leu Thr
            165                 170                 175

Cys Ser Gly Tyr Lys Val Ile His Cys Ser Gly Tyr Leu Lys Ile Arg
                180                 185                 190

Gln Tyr Met Leu Asp Met Ser Leu Tyr Asp Ser Cys Tyr Gln Ile Val
            195                 200                 205

Gly Leu Val Ala Val Gly Gln Ser Leu Pro Ser Ala Ile Thr Glu
    210                 215                 220

Ile Lys Leu Tyr Ser Asn Met Phe Met Phe Arg Ala Ser Leu Asp Leu
225                 230                 235                 240

Lys Leu Ile Phe Leu Asp Ser Arg Val Thr Glu Val Thr Gly Tyr Glu
                245                 250                 255

Pro Gln Asp Leu Ile Glu Lys Thr Leu Tyr His His Val His Gly Cys
            260                 265                 270

Asp Val Phe His Leu Arg Tyr Ala His His Leu Leu Val Lys Gly
    275                 280                 285

Gln Val Thr Thr Lys Tyr Tyr Arg Leu Leu Ser Lys Arg Gly Gly Trp
    290                 295                 300

Val Trp Val Gln Ser Tyr Ala Thr Val Val His Asn Ser Arg Ser Ser
305                 310                 315                 320

Arg Pro His Cys Ile Val Ser Val Asn Tyr Val Leu Thr Glu Ile Glu
                325                 330                 335

Tyr Lys Glu Leu Gln Leu Ser Leu Glu Gln Val Ser Thr Ala Lys Ser
            340                 345                 350

Gln Asp Ser Trp Arg Thr Ala Leu Ser Thr Ser Gln Glu Thr Arg Lys
            355                 360                 365

Leu Val Lys Pro Lys Asn Thr Lys Met Lys Thr Lys Leu Arg Thr Asn
    370                 375                 380

Pro Tyr Pro Pro Gln Gln Tyr Ser Ser Phe Gln Met Asp Lys Leu Glu
385                 390                 395                 400

Cys Gly Gln Leu Gly Asn Trp Arg Ala Ser Pro Ala Ser Ala Ala
            405                 410                 415

Ala Pro Pro Glu Leu Gln Pro His Ser Glu Ser Ser Asp Leu Leu Tyr
        420                 425                 430

Thr Pro Ser Tyr Ser Leu Pro Phe Ser Tyr His Tyr Gly His Phe Pro
        435                 440                 445

Leu Asp Ser His Phe Phe Ser Ser Lys Lys Pro Met Leu Pro Ala Lys
    450                 455                 460

Phe Gly Gln Pro Gln Gly Ser Pro Cys Glu Val Ala Arg Phe Phe Leu
465                 470                 475                 480

Ser Thr Met Pro Ala Ser Gly Glu Cys Gln Trp His Tyr Ala Asn Pro
                485                 490                 495

Leu Val Pro Ser Ser Ser Pro Ala Lys Asn Pro Glu Pro Pro
            500                 505                 510

Ala Asn Thr Ala Arg His Ser Leu Val Pro Ser Tyr Glu Gly Gly Ser
        515                 520                 525

Gly Leu Leu Val Gly Lys Val Gly Gly Leu Arg Thr Ala Gly Ser Arg
    530                 535                 540

Ser Ser His Gly Gly Gly Trp Gln Met Glu Thr Glu Pro Ser Arg Phe
545                 550                 555                 560
```

-continued

Gly Gln Thr Cys Pro Leu Ser Ala Ser Lys
        565                 570

<210> SEQ ID NO 5
<211> LENGTH: 567
<212> TYPE: DNA
<213> ORGANISM: Homo sapiens
<220> FEATURE:
<221> NAME/KEY: misc_feature
<222> LOCATION: (478)..(478)
<223> OTHER INFORMATION: n
<221> NAME/KEY: misc_feature
<222> LOCATION: (543)..(543)
<223> OTHER INFORMATION: n

<400> SEQUENCE: 5
ggaatattcg aaaccccgag cttttacaac ataaagcgca tggtgtggcc gcggcgggta      60
atggcgctct gggagccctg cccaggcggc ctctgctcgc cctcctccac ttccagctcc     120
gagctgggtg tgttgcaagt ttcatactcc tacatattat aagtgacact aatatcaggg     180
acaactaagt gctggggaac ttcaatgaaa acctggctgg taaagtcaac accccagac     240
ttctctgtgc tacatttctt taattaattc cggagtggtg tgtggacggg cgtctttgca     300
gttattatac acgtaagtga attaggccat ttgaagctac gaagtcatac ccaacatttt     360
ccattaagaa tattattttt ttagctactg ctggcaactt ttagaattta attatgataa     420
ttttcctctt ttcctcatta tcccagatat ggctggttgt gagatacttt ttcactanat     480
gtgtctttt aatgattttg gaattaagca agtatgccaa atgcgccaag acatttataa     540
ctntagaaat tgctgtatag tatatat                                         567

<210> SEQ ID NO 6
<211> LENGTH: 1001
<212> TYPE: DNA
<213> ORGANISM: Homo sapiens

<400> SEQUENCE: 6
ggaatattcg aaaccccgag cttttacaac ataaagcgca tggtgtggcc gcggcgggta      60
atggcgctct gggagccctg cccaggcggc ctctgctcgc cctcctccac ttccagctcc     120
gagctgggtg tgttgcaagt ttcatactcc tacatattat aagtgacact aatatcaggg     180
acaactaagt gctggggaac ttcaatgaaa acctggctgg taaagtcaac accccagac     240
ttctctgtgc tacatttctt taattaattc cggagtggtg tgtggacggg cgtctttgca     300
gttattatac acgtaagtga attaggccat ttgaagctac gaagtcatac ccaacatttt     360
ccattaagaa tattattttt ttagctactg ctggcaactt ttagaattta attatgataa     420
ttttcctctt ttcctcatta tcccagatat ggctggttgt gagatacttt ttcactaaat     480
gtgtctttt aatgattttg gaattaagca agtatgccaa atgcgccaag acatttataa     540
ctttagaaat tgctgtatag tatatatttt tggaacacca caggtttagt tgggaaaata     600
ttttgcagct gagttagaaa cttgaaagtt aggcttataa tcaagatgct gattttcaac     660
cttagcatcg gggaaggtaa tgatagttta gttggcaaag acttttttgca gcaaactgta     720
tttgagacag cagaatccaa ggatatcttt caagattcac ttatactaca ttctttttag     780
cccctctct aggggtggag gggtggctt agaaaaacca aagtaatct ggtttcaatt     840
acatgctgta aaatagaat tgtggccag aaattaattt ggaatatttt ttatgggggc     900
aacattgtgg gttgtatgag tctttcacca actttattgc ttttcttgg ttctggatct     960
aaaatatgaa tgagtaaata aaatacagtt tccttttttca a                      1001

<210> SEQ ID NO 7
<211> LENGTH: 22
<212> TYPE: DNA
<213> ORGANISM: Homo sapiens

<400> SEQUENCE: 7
tggaggaccg ccttgtctac ct                                              22

<210> SEQ ID NO 8
<211> LENGTH: 20
<212> TYPE: DNA
<213> ORGANISM: Homo sapiens

<400> SEQUENCE: 8
ccggtggctc tggaggattt                                                 20

<210> SEQ ID NO 9
<211> LENGTH: 20
<212> TYPE: DNA
<213> ORGANISM: Homo sapiens

<400> SEQUENCE: 9
accttctgta cacgccatcc                                                 20

<210> SEQ ID NO 10
<211> LENGTH: 472
<212> TYPE: DNA
<213> ORGANISM: Homo sapiens

<400> SEQUENCE: 10
tggaggaccg ccttgtctac ctcacaagaa actaggaaat tagtgaaacc caaaaatacc      60
aagatgaaga caaagctgag aacaaaccct tacccccac agcaatacag ctcgttccaa      120
atggacaaac tggaatgcgg ccagctcgga aactggagag ccagtccccc tgcaagcgct     180
gctgctcctc cagaactgca gccccactca gaaagcagtg accttctgta cacgccatcc     240
tacagcctgc ccttctccta ccattacgga cacttccctc tggactctca cgtcttcagc     300
agcaaaaagc caatgttgcc ggccaagttc gggcagcccc aaggatcccc ttgtgaggtg     360
gcacgctttt tcctgagcac actgccagcc agcggtgaat gccagtggca ttatgccaac     420
cccctagtgc ctagcagctc gtctccagct aaaaatcctc cagagccacc gg             472

<210> SEQ ID NO 11
<211> LENGTH: 24
<212> TYPE: DNA
<213> ORGANISM: Homo sapiens

<400> SEQUENCE: 11
attcttggac ttctccttca tcgc                                            24

<210> SEQ ID NO 12
<211> LENGTH: 24
<212> TYPE: DNA
<213> ORGANISM: Homo sapiens

<400> SEQUENCE: 12
gagagcaaga aagcacagca agcc                                            24

<210> SEQ ID NO 13
<211> LENGTH: 24
<212> TYPE: DNA

```
<213> ORGANISM: Homo sapiens

<400> SEQUENCE: 13
ccgaacgaca cgaaagaacg agag                                              24

<210> SEQ ID NO 14
<211> LENGTH: 15
<212> TYPE: PRT
<213> ORGANISM: Homo sapiens

<400> SEQUENCE: 14

Ser His Gly Gly Gly Trp Gln Met Glu Thr Glu Pro Ser Arg Phe
1               5                   10                  15

<210> SEQ ID NO 15
<211> LENGTH: 22
<212> TYPE: DNA
<213> ORGANISM: Homo sapiens

<400> SEQUENCE: 15
tggaggaccg ccttgtctac ct                                                22

<210> SEQ ID NO 16
<211> LENGTH: 24
<212> TYPE: DNA
<213> ORGANISM: Homo sapiens

<400> SEQUENCE: 16
gcccaaagcg tgagggttct gtct                                              24
```